(12) United States Patent
Prasad et al.

(10) Patent No.: US 9,283,314 B2
(45) Date of Patent: Mar. 15, 2016

(54) CANNULA SYSTEMS

(75) Inventors: Jayanthi G. Prasad, Lexington, MA (US); Farhad Zarinetchi, Chelmsford, MA (US); Emmanuel N. Ilongo, Lynn, MA (US)

(73) Assignee: ABIOMED, INC., Danvers, MA (US)

( * ) Notice: Subject to any disclaimer, the term of this patent is extended or adjusted under 35 U.S.C. 154(b) by 1472 days.

(21) Appl. No.: 11/232,451

(22) Filed: Sep. 21, 2005

(65) Prior Publication Data

US 2007/0066943 A1  Mar. 22, 2007

(51) Int. Cl.
*A61M 1/12* (2006.01)
*A61M 1/36* (2006.01)
*A61B 17/00* (2006.01)
*A61B 17/34* (2006.01)
*A61M 1/10* (2006.01)

(52) U.S. Cl.
CPC ............ *A61M 1/3653* (2013.01); *A61M 1/1008* (2014.02); *A61M 1/122* (2014.02); *A61M 1/3659* (2014.02); *A61B 2017/00247* (2013.01); *A61B 2017/00252* (2013.01); *A61B 2017/3425* (2013.01); *A61M 1/10* (2013.01)

(58) Field of Classification Search
CPC ............ A61M 1/1008; A61M 1/3653; A61M 1/3659; A61M 1/122; A61M 1/10; A61B 17/3421; A61B 17/11; A61B 17/3496; A61B 2017/1132; A61B 17/1135; A61B 17/1139; A61B 17/3425; A61B 17/00247; A61B 17/00252
USPC ......... 606/153, 155, 156, 108, 184, 185, 179, 606/182, 167; 623/1.23, 1.31; 600/16, 573, 600/577; 604/8, 506, 507, 164.11, 164.12, 604/264, 272, 104–109, 46, 47, 6.05, 6.06, 604/523, 525, 268, 198, 403–416
See application file for complete search history.

(56) References Cited

U.S. PATENT DOCUMENTS

| | | | | | |
|---|---|---|---|---|---|
| 2,673,561 | A | * | 3/1954 | Peterson, Jr. | 604/216 |
| 2,792,199 | A | * | 5/1957 | Becker et al. | 175/211 |
| 2,847,995 | A | * | 8/1958 | Adams | 604/198 |
| 3,134,380 | A | * | 5/1964 | Armao | 604/198 |
| 3,339,435 | A | * | 9/1967 | Walter-Helmut | 408/67 |
| 3,536,149 | A | * | 10/1970 | Laird | 175/209 |

(Continued)

FOREIGN PATENT DOCUMENTS

EP  1 462 133 A2  9/2004
WO  WO 01/05447 A1  1/2001

(Continued)

OTHER PUBLICATIONS

Ventricular/Atrial Cannulation Sewing Cuff, "Instructions for Use," ABIOMED, Inc., Document No. 0507-9100B, Aug. 2004, 1 pg.

(Continued)

*Primary Examiner* — Christopher L Templeton
(74) *Attorney, Agent, or Firm* — Ropes & Gray LLP

(57) ABSTRACT

Systems and methods for coupling devices such as a ventricular assist device to vascular tissues, such as a heart. In one version, a method is provided for attaching a device to vascular tissue for fluid flow. The device includes a cannula coupled to a cuff, and the method includes coupling the cuff to the vascular tissue, penetrating the vascular tissue by inserting a penetration device through the cannula, and inserting a first end of the cannula through the cuff and into the vascular tissue.

4 Claims, 22 Drawing Sheets

(56) References Cited

U.S. PATENT DOCUMENTS

| | | | | |
|---|---|---|---|---|
| 3,583,821 A | * | 6/1971 | Shaub et al. | 408/72 R |
| 3,776,647 A | * | 12/1973 | Hart | 408/241 G |
| 3,788,328 A | | 1/1974 | Alley et al. | |
| 3,884,230 A | * | 5/1975 | Wulff | 604/198 |
| 3,905,375 A | * | 9/1975 | Toyama | 606/189 |
| 4,564,054 A | * | 1/1986 | Gustavsson | 141/329 |
| 4,670,008 A | * | 6/1987 | Von Albertini | 604/165.01 |
| 4,725,267 A | * | 2/1988 | Vaillancourt | 604/192 |
| 4,769,031 A | * | 9/1988 | McGough et al. | 623/1.37 |
| 4,775,369 A | * | 10/1988 | Schwartz | 604/263 |
| 4,782,841 A | * | 11/1988 | Lopez | 600/577 |
| 4,795,432 A | * | 1/1989 | Karczmer | 604/110 |
| 4,892,521 A | * | 1/1990 | Laico et al. | 604/192 |
| 4,927,416 A | * | 5/1990 | Tomkiel | 604/198 |
| 4,944,729 A | | 7/1990 | Buckberg et al. | |
| 4,994,027 A | | 2/1991 | Farrell | |
| 4,998,921 A | * | 3/1991 | Vickroy et al. | 604/167.02 |
| 5,011,469 A | | 4/1991 | Buckberg et al. | |
| 5,015,240 A | * | 5/1991 | Soproni et al. | 604/192 |
| 5,015,242 A | * | 5/1991 | Heifetz | 604/198 |
| 5,061,123 A | * | 10/1991 | Broussard | 408/67 |
| 5,084,064 A | | 1/1992 | Barak et al. | |
| 5,135,489 A | | 8/1992 | Jepson et al. | |
| 5,151,087 A | | 9/1992 | Jonkman | |
| 5,160,230 A | * | 11/1992 | Cuevas | 408/67 |
| 5,197,971 A | | 3/1993 | Bonutti | |
| 5,219,338 A | * | 6/1993 | Haworth | 604/198 |
| 5,239,982 A | * | 8/1993 | Trauthen | 600/117 |
| 5,250,031 A | * | 10/1993 | Kaplan et al. | 604/110 |
| 5,267,974 A | * | 12/1993 | Lambert | 604/195 |
| 5,290,254 A | * | 3/1994 | Vaillancourt | 604/192 |
| 5,292,210 A | * | 3/1994 | Nowick | 408/67 |
| 5,295,963 A | * | 3/1994 | Deeks | 604/110 |
| 5,295,972 A | * | 3/1994 | Mischenko | 604/192 |
| 5,312,371 A | * | 5/1994 | Dombrowski et al. | 604/198 |
| 5,328,483 A | * | 7/1994 | Jacoby | 604/185 |
| 5,401,244 A | | 3/1995 | Boykin et al. | |
| 5,470,320 A | | 11/1995 | Tiefenbrun et al. | |
| 5,527,297 A | * | 6/1996 | Paul | 604/263 |
| 5,554,131 A | * | 9/1996 | Lacivita | 604/198 |
| RE35,459 E | | 2/1997 | Jonkman | |
| 5,645,530 A | * | 7/1997 | Boukhny et al. | 604/22 |
| 5,653,561 A | * | 8/1997 | May | 408/67 |
| 5,713,874 A | * | 2/1998 | Ferber | 604/198 |
| 5,720,726 A | | 2/1998 | Marcadis et al. | |
| 5,765,654 A | * | 6/1998 | Burger | 175/211 |
| 5,769,826 A | | 6/1998 | Johnson et al. | |
| 5,858,009 A | | 1/1999 | Jonkman | |
| 5,882,344 A | | 3/1999 | Stouder, Jr. | |
| 5,885,255 A | * | 3/1999 | Jaeger et al. | 604/192 |
| 5,894,015 A | * | 4/1999 | Rechtin | 422/301 |
| 5,911,728 A | | 6/1999 | Sepetka et al. | |
| 6,042,576 A | | 3/2000 | DeVries | |
| 6,063,114 A | * | 5/2000 | Nash et al. | 623/1.36 |
| 6,110,185 A | | 8/2000 | Barra et al. | |
| 6,120,494 A | | 9/2000 | Jonkman | |
| 6,126,675 A | | 10/2000 | Shchervinsky et al. | |
| 6,146,325 A | | 11/2000 | Lewis et al. | |
| 6,146,371 A | | 11/2000 | DeWindt et al. | |
| 6,186,999 B1 | | 2/2001 | Chen | |
| 6,190,357 B1 | | 2/2001 | Ferrari et al. | |
| 6,238,371 B1 | * | 5/2001 | Himbert et al. | 604/187 |
| 6,241,743 B1 | * | 6/2001 | Levin et al. | 606/153 |
| 6,290,683 B1 | * | 9/2001 | Erez et al. | 604/273 |
| 6,319,231 B1 | | 11/2001 | Andrulitis | |
| 6,468,249 B1 | * | 10/2002 | Steyn | 604/192 |
| 6,582,388 B1 | | 6/2003 | Coleman et al. | |
| 6,613,062 B1 | | 9/2003 | Leckrone et al. | |
| 6,695,822 B2 | * | 2/2004 | Adams et al. | 604/268 |
| 6,726,648 B2 | | 4/2004 | Kaplon et al. | |
| 6,790,220 B2 | | 9/2004 | Morris et al. | |
| 6,802,806 B2 | | 10/2004 | McCarthy et al. | |
| 6,846,296 B1 | | 1/2005 | Milbocker et al. | |
| 6,858,001 B1 | | 2/2005 | Aboul-Hosn | |
| 6,884,224 B2 | * | 4/2005 | Dalton | 600/573 |
| 7,214,234 B2 | * | 5/2007 | Rapacki et al. | 606/167 |
| 2001/0041902 A1 | * | 11/2001 | Lepulu et al. | 606/153 |
| 2002/0045846 A1 | | 4/2002 | Kaplon et al. | |
| 2002/0045862 A1 | | 4/2002 | Briscoe et al. | |
| 2002/0082614 A1 | * | 6/2002 | Logan et al. | 606/139 |
| 2003/0171695 A1 | * | 9/2003 | Zurcher | 600/577 |
| 2004/0002624 A1 | | 1/2004 | Yu et al. | |
| 2004/0059178 A1 | | 3/2004 | McCarthy et al. | |
| 2004/0199111 A1 | | 10/2004 | Gershowitz | |
| 2004/0236170 A1 | | 11/2004 | Kim | |
| 2005/0192604 A1 | * | 9/2005 | Carson et al. | 606/153 |
| 2005/0251187 A1 | * | 11/2005 | Beane et al. | 606/180 |
| 2005/0283222 A1 | * | 12/2005 | Betelia et al. | 623/1.11 |
| 2006/0184189 A1 | * | 8/2006 | Olson et al. | 606/181 |
| 2008/0161826 A1 | * | 7/2008 | Guiraudon | 606/108 |

FOREIGN PATENT DOCUMENTS

| | | |
|---|---|---|
| WO | WO 03/001980 A2 | 1/2003 |
| WO | WO 2004/078234 A2 | 9/2004 |
| WO | WO 2004/082742 A1 | 9/2004 |

OTHER PUBLICATIONS

Kalangos et al., "Conversion from Routine CPB to Centrifugal Mechanical Assist by Transaortic Inflow Cannulation of the Left Ventricle," Ann Thorac Sug 1998, 65:1168-70.

Wyatt, et al., "Use of a Dacron Cuff to Decrease Bleeding from Atrial Cannulas of Ventricular Assist Devices," vol. 65, No. 4, Apr. 1998, pp. 1264-1265.

Clinical Reference Manual—Circulatory Support Systems, ABIOMED, Jun. 2004, pp. 68.

Invitation to Pay Additional Fees with Partial International Search Report for PCT/US2006/036586 mailed Feb. 13, 2007.

International Search Report for PCT/US2006/036586 mailed Jun. 12, 2007.

* cited by examiner

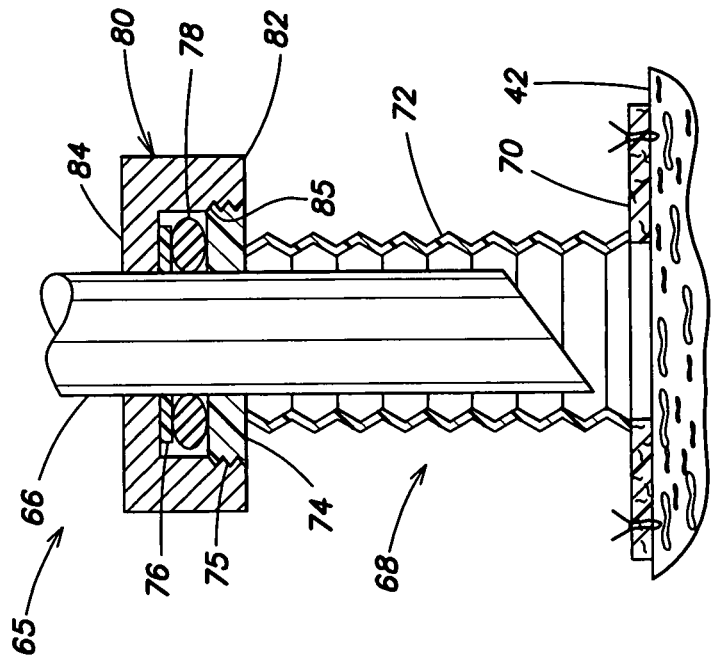
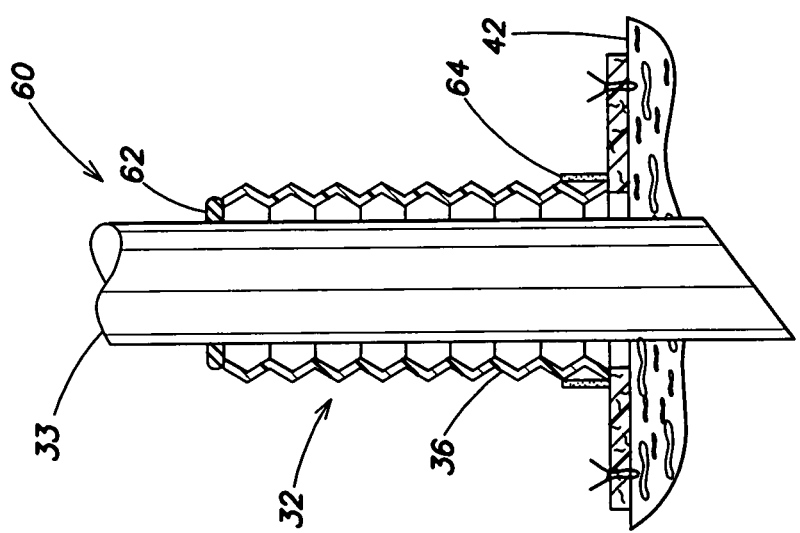
FIG. 13
FIG. 12

CANNULA SYSTEMS

BACKGROUND OF INVENTION

1. Field of Invention

Embodiments of the invention relate generally, but are not limited to, cannula systems and methods of using a cannula with, for example, ventricular assist devices.

2. Discussion of Related Art

The use of a ventricular assist device (VAD) in patients suffering from damaged heart tissue or heart failure is known. A ventricular assist device may be used as a permanent solution for a patient, or may be used as a short-term solution while a patient is waiting for a heart transplant. VAD's may also be used to provide damaged heart muscle with the opportunity for rest to increase the probability of healing of the heart muscle, after which the VAD may be removed. Typically, a VAD is used to assist the left ventricle of the heart by drawing blood from the left ventricle, and pumping blood into the aorta.

FIG. 1 provides a diagram of a typical ventricular assist device 10 coupled to the heart 12 and the aorta 14 of a patient. The VAD 10 is coupled to the ventricle 13 of the heart using an inflow cannula 16 and is coupled to the aorta using an outflow cannula 18. VAD devices like that shown in FIG. 1 are available from ABIOMED, Inc. of Danvers, Mass., under the trade names BVS® 5000 Bi-Ventricular Support System and AB5000™ Circulatory Support System.

Typically, an inflow cannula is coupled to the heart tissue using purse string sutures in a well-known manner. When used properly, such purse string sutures provide an effective seal for the cannula to the heart, however, the sutures can loosen over time, require skill to install, and typically require opening of the chest cavity for installation and removal.

SUMMARY OF INVENTION

At least some embodiments of the invention are directed to systems and methods for coupling devices, such as a ventricular assist device, to vascular tissues, such as the heart. Further, at least some embodiments of the present invention are directed to ventricular coupling devices, such as a cannula that are compatible with minimally invasive surgical procedures.

One aspect of the invention is directed to a method for attaching a device to vascular tissue for fluid flow, wherein the device includes a cannula assembly that includes a cannula coupled to a cuff. The method includes coupling the cuff to the vascular tissue, penetrating the vascular tissue by inserting a penetration device through the cannula, and inserting a first end of the cannula through the cuff and into the vascular tissue.

The method may further include coupling a second end of the cannula to an external device and passing fluid through the cannula between the external device and the vascular tissue. The method may also include removing the cannula from the vascular tissue, and cutting and sealing a graft portion of the cuff. Inserting the first end of the cannula may include inserting the cannula into the heart of a patient. The cuff may include a substantially planar section and an elongated section coupled to the planar section and coupled to the cannula, and coupling the cuff may include attaching the planar section to the vascular tissue. In the method, Inserting a first end of the cannula may include collapsing the elongated section of the cuff. The method may further include determining a depth of insertion of the cannula into the vascular tissue. The cannula may be coupled to the cuff using a slideable seal, and inserting a first end of the cannula may include sliding the cannula with respect to the seal. In the method, coupling the cuff to the vascular tissue may include using a latching mechanism to couple the cuff to the cannula, and the method may further include removing the cannula from the vascular tissue and uncoupling the latching mechanism. In the method, removing the cannula may include sliding the cannula with respect to the seal until a stop mechanism included on at least one of the cannula, the cuff and the slideable seal prevents further withdrawal of the cannula. Removing the cannula may include snapping a portion of the cannula into the stop mechanism. The method may further include coupling sutures to the cuff, and after inserting the cannula into the vascular tissue, securing the cannula to the cuff using the sutures. The method may still further include using at least one tourniquet to secure the sutures and securing the at least one tourniquet to the cannula assembly.

Another aspect of the invention is directed to a method of coupling a cannula system to vascular tissue. The method includes coupling a first portion of a cuff to the vascular tissue, the cuff having a second portion that includes a cuff connector, coupling a cannula assembly that includes a cannula and a cannula connector to the cuff by mating the cannula connector with the cuff connector, and inserting the cannula through the cuff and into the vascular tissue.

The method may further include applying a pressurized fluid or gas to an inner portion of the cuff to test integrity of a seal between the first portion of the cuff and the vascular tissue. In the method, applying a pressurized fluid or gas may include coupling a pressure testing assembly to the cuff by mating a connector of the pressure testing assembly with the cuff connector, and inserting the cannula may include inserting the cannula into the heart of a patient. The method may further include coupling a stylet assembly to the cuff by mating a connector of the stylet assembly with the cuff connector, and using the stylet assembly to pierce a surface of the vascular tissue. The method may still further include detecting that the vascular tissue has been at least partially pierced, and further moving the stylet assembly to fully pierce the vascular tissue. The stylet assembly may include a hypodermic needle, and the method of detecting may include drawing blood through the hypodermic needle. The stylet assembly may include an adjustment device, and the method may further include manipulating the adjustment device to move a piercing surface of the stylet assembly towards the vascular tissue. The method may further include withdrawing the piercing surface from the vascular tissue and decoupling the stylet assembly from the cuff assembly. The cannula may be coupled to the cannula assembly such that the cannula can slide with respect to the cannula connector, and the method may further include sliding a first end of the cannula through the cuff and into the vascular tissue. The method may further include coupling a second end of the cannula to an external device, passing fluid through the cannula between the external device and the vascular tissue, removing the cannula from the vascular tissue, and cutting and sealing a graft portion of the cuff. Removing the cannula may include sliding the cannula until a stop mechanism included in the cannula assembly prevents further withdrawal of the cannula. The method may include snapping a portion of the cannula into the stop mechanism. In the method, inserting the cannula may include inserting the cannula into the left ventricle of the patient and the method may further include after inserting the cannula, closing a surgical opening in the chest of the patient. In the method, removing the cannula may include using minimally invasive surgery without performing a sternotomy. The cannula assembly may include an extraction device, and removing the cannula may include using the extraction device to withdraw the cannula from the ventricle of the patient.

Yet another aspect of the invention is directed to a cannula system. The cannula system includes a cuff having a first section to couple to vascular tissue and having a second section coupled to the first section, wherein the second section includes an elongated section having an inner portion, and a cannula fixed to the second section of the cuff such that fluid can flow from vascular tissue through the inner portion of the second section and into the cannula.

In the cannula system, the cannula may be fixed to the cuff using an adhesive. The cannula system may further include a depth gauge coupled to the second section of the cuff, and the depth gauge may include a transparent tube positioned over the second portion of the cuff. The cannula may be fixed to the second section using a slideable seal configured such that the cannula can move within the slideable seal for insertion into vascular tissue. The slideable seal may include a latching mechanism coupled to one of the second section and the cannula that mates with a mating portion on the other of the second section and the cannula. The cannula system may further include an adapter having a stopping mechanism to limit motion of the cannula within the slideable seal. The stopping mechanism may include a convex ring on the cannula that mates with an annular section of the slideable seal. The cannula system may further include at least one suture coupled to the cuff to secure the cuff to the cannula after insertion of the cannula into the vascular tissue, and at least one tourniquet coupled to the at least one suture.

Another aspect of the invention is directed to a cannula system. The cannula system includes a cuff having a first section to couple to vascular tissue, a second section coupled to the first section, and a cuff connector coupled to the second section, wherein the second section includes an elongated section having an inner portion, and a cannula assembly including a cannula having a connector that is configured to mate with the cuff connector such that when mated fluid can flow through the inner portion of the second section and into the cannula.

The cannula system may further include a pressure testing mechanism having a first connector configured to mate with the cuff connector and having a second connector adapted to mate with a source of pressurized fluid or gas. The cannula system may include a stylet assembly having at least one cutting device for piercing vascular tissue, and having a connector configured to mate with the cuff connector. The stylet assembly may be configured to provide a fluid seal with the cuff to prevent fluid loss from the cannula system. The stylet assembly may include a fluid detector to provide an indication of penetration of vascular tissue by the at least one cutting device. The fluid detector may include a hypodermic needle coupled to the at least one cutting device and in fluid communication with a transparent section of the stylet assembly. The stylet assembly may further include a rotable knob coupled to the at least one cutting device and configured to move the at least one cutting device upon rotation of the rotatable knob. The cannula assembly may include a slideable seal coupled to the connector of the cannula and configured such that the cannula can move within the slideable seal for insertion into vascular tissue. The cannula system may further include an adapter having a stopping mechanism to limit motion of the cannula within the slideable seal. The stopping mechanism may include a convex ring on the cannula that mates with an annular section of the slideable seal. The cannula system may further include a retraction device coupled to the cannula and configured to extend from a patient's body when the cannula system is coupled to vascular tissue of a patient. The retraction device may include a cord coupled to the cannula.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 12 is a cross-sectional side view of a cannula assembly in accordance with another embodiment;

FIG. 13 is a cross-sectional side view of a cannula assembly in accordance with yet another embodiment;

DETAILED DESCRIPTION

Figure 1:
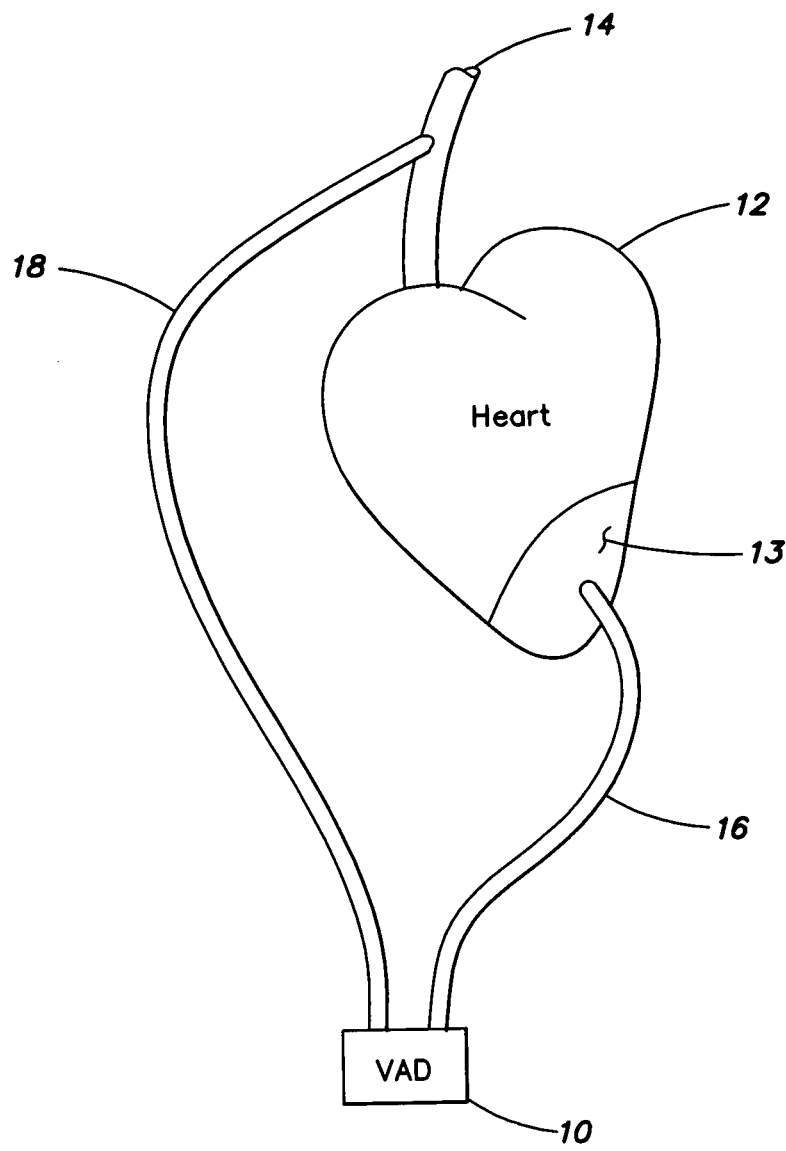
FIG. 1 is a functional block diagram showing the coupling of a ventricular assist device to the heart using an inflow cannula and an outflow cannula.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

At least some embodiments of the invention provide an improved cannula, accessories for use with cannulae, as well as methods of inserting and removing cannulae from vascular tissue, such as heart tissue. In at least one embodiment, an improved inflow cannula for use with, for example, a VAD like that of FIG. 1, is provided along with methods for insertion and removal of the cannula as well as devices and accessories for use with the cannula. At least some embodiments of the invention provide devices, such as a cannula, that may be removed from patients using minimally invasive surgical techniques. Embodiments of the invention may be designed for use with and coupled to vascular tissue in addition to heart tissue. As used herein, vascular includes any body passageway or tissue of the circulatory system, lymph system, gastrointestinal system, etc, and includes, for example, arteries, veins, lymph ducts, intestines, urethra, heart muscle, etc. In descriptions provided below, reference is made to distal and proximal ends of a cannula and related devices. For purposes of description, the distal end refers to the end of the cannula that enters the body, for example, the left ventricle, while proximal end refers to the end of the cannula that connects to, for example, a ventricular assist device.

Figure 2:
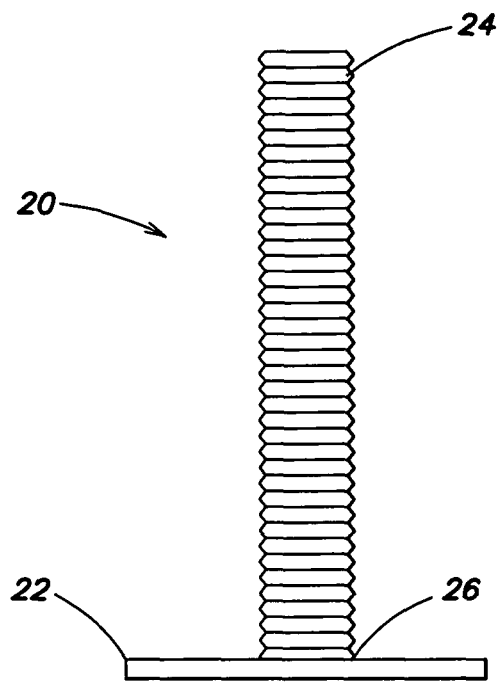
FIG. 2 is a side view of a sewing cuff that may be used with at least one embodiment of the present invention.
Figure 3:
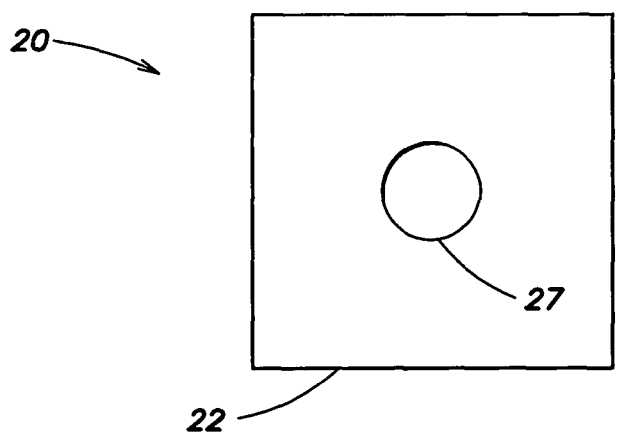
FIG. 3 is a top view of the sewing cuff of FIG. 2.
Figure 4:
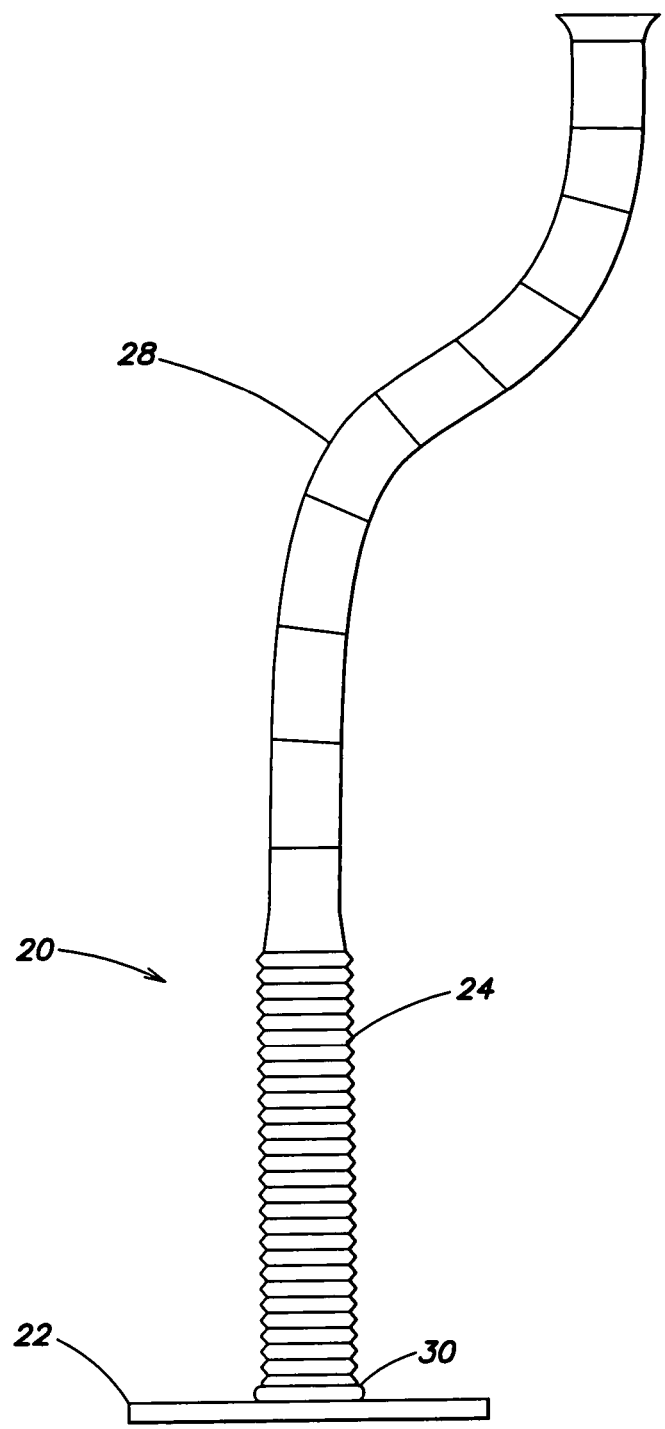
FIG. 4 is a side view of the cuff of FIG. 2 coupled to a cannula.

A sewing cuff 20 useful, for example, with VAD systems, will now be described with reference to FIGS. 2, 3 and 4, which respectively show a side view of the sewing cuff 20, a top view of the sewing cuff 20, and a side view of the cuff attached to an inflow cannula 28. The sewing cuff includes a patch section 22 and a graft section 24. The patch section is sewn to the graft section at a junction 26, using, for example, surgical thread. In one version, the patch section 22 is constructed from 0.5 mm thick PTFE (TEFLON®) felt, and the graft section 24 is constructed using IMPRA® graft material available from Bard Peripheral Vascular, Inc. of Tempe Ariz., coated with a medical-grade silicone. In other embodiments, other materials may be used for the graft section and the patch section, including HEMASHIELD® material available from Boston Scientific, Inc. of Natick, Mass. In one embodiment, designed for use with a 42 Fr cannula the graft section is approximately three inches in length and has an inner diameter of 0.46 inches. As shown in FIG. 2, in at least one embodiment, the graft section is constructed in an accordion/pleated manner, as is known, such that the graft section can be stretched or compressed easily. The patch section 22 has a center hole 27 also having a diameter of 0.46 inches. Depending on the particular application and the particular cannula being used, the cuff may be smaller or larger and with a smaller or larger inner diameter. Sewing cuffs like that shown in FIG. 1 are available from Abiomed, Inc. under, for example, part no. 0507-0042.

As will now be described with reference to FIG. 4, the sewing cuff 20 may be used with existing cannulae, such as cannula 28, to simplify the implantation and explantation of the cannulae and reduce the likelihood of significant blood loss during such procedures. During implantation, the sewing cuff is first coupled to, for example, the left ventricle. The patch section may be coupled to the left ventricle using sutures, using glue, or using arrays of gripping elements, such as hooks or barbs, as disclosed in U.S. Pat. No. 6,846,296 to Milbocker et al., which is incorporated herein by reference.

Once the sewing cuff is in place, the left ventricle is pierced using one of a number of different devices known to those skilled in the art by passing the piercing device through the graft section 24 with the left ventricle being pierced at the opening of the patch section 22. After the ventricle is pierced, the distal end of a catheter is inserted through the graft section and into the left ventricle. The proximal end of the catheter is either coupled to a device such as a VAD, or is sealed or clamped pending connection to a VAD. The graft section 24 of the cuff 22 is sealed to the catheter at a sealing junction 30 using, for example, purse string sutures. The seal 30 holds the cannula in place in the sewing cuff.

When it is desired to remove the catheter from the patient, the purse string sutures coupling the catheter to the graft section are cut, and the catheter is withdrawn from the graft section. The opening in the graft section may then be tied off, clamped, or stapled to provide a seal over the opening in the left ventricle. The cuff may then be left attached to the heart. Use of the sewing cuff provides several advantages including the ability to remove a cannula from a patient's left ventricle simply without the need for sutures, and because there is no need for sutures, minimally invasive techniques may be used to remove the cannula.

Figure 5:
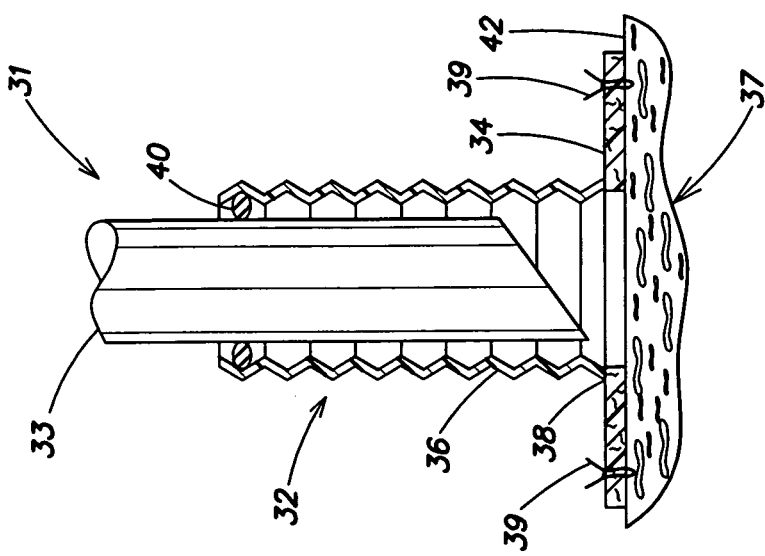
FIG. 5 is a cross-sectional side view of a cannula assembly coupled to the surface of a heart in accordance with one embodiment.

As will now be discussed with reference to FIG. 5, one embodiment of the invention is directed to a cannula assembly 31 having an apical sewing cuff 32 with a cannula 33 attached thereto. The embodiment of FIG. 5 differs from sewing cuffs discussed above in that, among other things, the cannula 33 is coupled to the sewing cuff 32 prior to attachment of the sewing cuff to the heart or other vascular tissue. The sewing cuff 32 may be substantially similar to the sewing cuff 20 discussed above and includes a patch section 34 attached to a graft section 36 at a seam 38. In one embodiment, the cannula 33 is a 42 Fr cannula constructed of PVC or polyurethane, however, other cannulae may be used in other embodiments of the invention. In FIG. 5, the patch section 34 is shown coupled to a surface 42 of a heart using sutures 39 or other devices as discussed above.

As shown in FIG. 5, the graft section of the sewing cuff is coupled to the cannula 33 at a seal 40. The seal 40 may be implemented in one of a number of ways including using purse string sutures, glue, such as Bioglue® adhesive available from Cryolife, Inc. of Kennesaw, Ga., fibrin glue, or in any other manner that provides a seal between the graft section and the cannula. FIG. 5 shows the distal end of the cannula 33 with the patch section of the cuff 32 coupled to a surface 42 of a heart.

Figure 6:
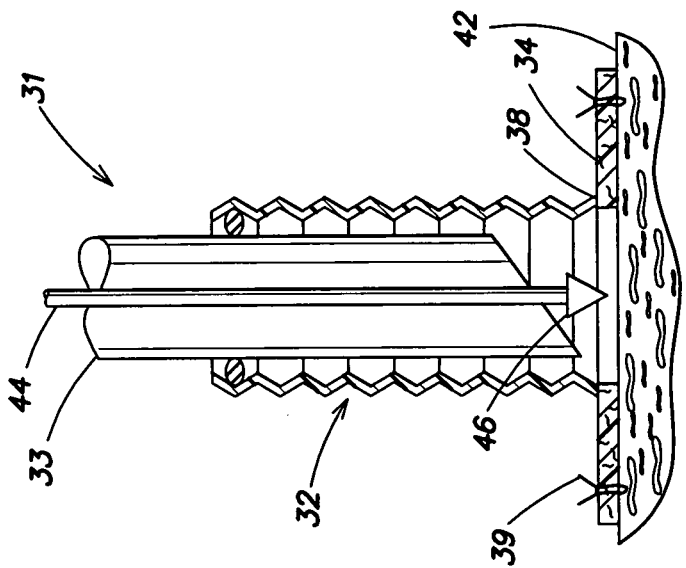
FIG. 6 is a cross-sectional side view of the cannula assembly of FIG. 5 in conjunction with a tool used with the assembly to pierce the surface of the heart.

Implantation and removal of the cannula 33 will now be described with reference to FIGS. 6-9. As shown in FIG. 6, an insertion tool 44 having a blade 46 is inserted through the cannula 33 to puncture the heart tissue. Prior to inserting the tool 44, the cannula may be filled with saline solution to remove all air from the cannula. The insertion tool may be sealed to the cannula and/or the graft section to prevent the saline solution and any blood from escaping the cannula as the insertion of the blade is made into the heart. After the surface of the heart is pierced, the insertion tool is removed from the cannula 33, and the proximal end of the cannula may be clamped or coupled to a VAD to prevent any leakage from the cannula.

Figure 7:
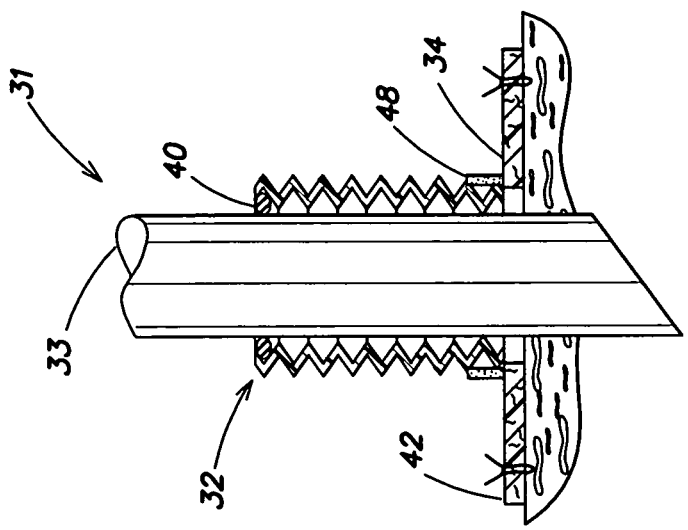
FIG. 7 is a cross-sectional side view of the cannula assembly of FIG. 5 with a cannula of the assembly shown in position in the ventricle of a heart.

As shown in FIG. 7, the cannula is then inserted through the surface 42 of the heart and into, for example, the left ventricle. As the cannula 33 is inserted, the graft section 36 of the sewing cuff 32 is compressed as shown in FIG. 7. Once the cannula is inserted to the desired depth, umbilical tape 48 is wrapped tightly around the outside of the graft section of the cuff to secure the cannula in place in the heart.

Figure 8:
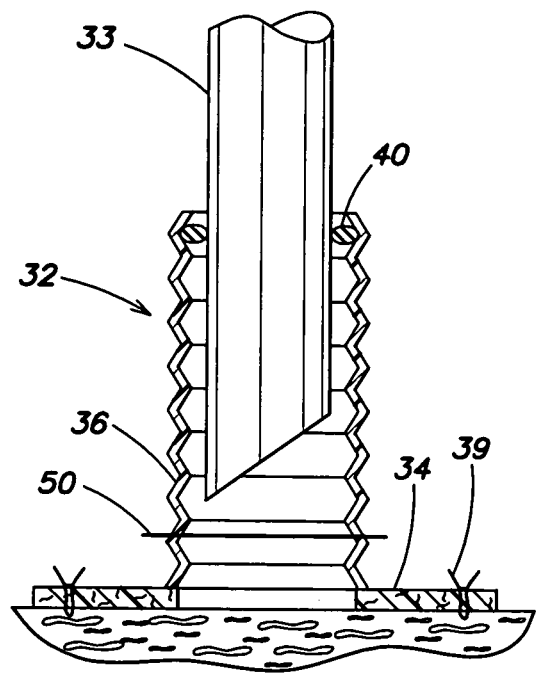
FIGS. 8 and 9 demonstrate a process for removal of the cannula assembly of FIG. 5.
Figure 9:
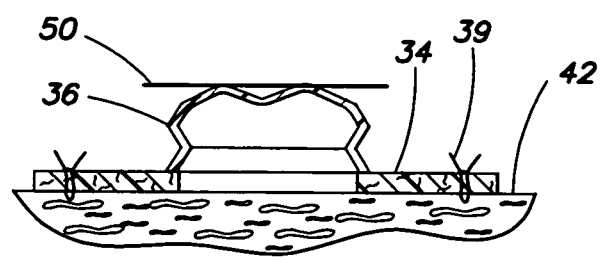

To extract the cannula 33, the umbilical tape is cut, the cannula is withdrawn from the heart, and the graft section of the sewing cuff is cut at a point 50 below the cannula as shown in FIG. 8. After the graft section is cut, the cannula can be completely removed from the chest. The sewing cuff 32 may be stapled, sewn or glued at the point at which it is cut, and the remainder of the sewing cuff, 32 may be left attached to the heart as shown in FIG. 9. In one embodiment an ENDO GIA® surgical stapler available from Tyco Healthcare of Mansfield, Mass. may be used to staple the sewing cuff 32. In one embodiment, the staples used may be 35 mm staples having 2.0 to 2.5 mm legs.

In at least some embodiments of the invention described above and below, after implantation of a cannula, the chest cavity of the patient may be closed, and the cannula can be later removed using minimally invasive techniques that do not require a second opening of the chest cavity. Further, at least some embodiments provide for implantation and removal of cannulae in a controlled manner without exposing the patient and the surgeon to a risk of sudden loss of control over bleeding.

Figure 10:
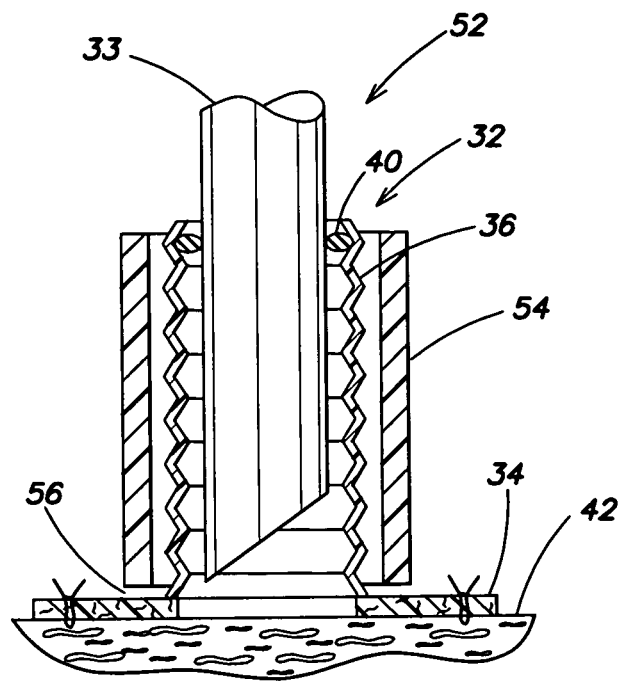
FIGS. 10 and 11 demonstrate the use of a cannula assembly in accordance with another embodiment.
Figure 11:
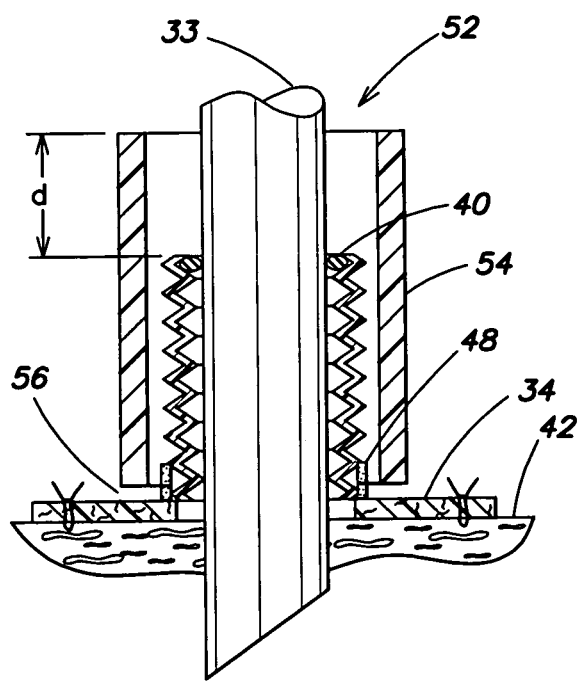

In another embodiment of the invention which will now be described with reference to FIGS. 10 and 11, a cannula assembly 52, which is similar in many aspects to cannula assembly 31, is provided. The cannula assembly 52 includes the sewing cuff 32 and the cannula 33, attached in a manner similar to that described above for cannula assembly 31. In addition, cannula assembly 52 includes a depth gauge 54 that is used to determine the depth of the cannula into the heart. In one embodiment, the depth gauge 54 includes a cylindrical transparent plastic tube that extends from a location just above the joint between the graft section 36 and the patch section 34 of the cuff 32 to the top of the graft section. In one embodiment, the bottom of the depth gauge 54 is glued to the graft section using, for example BIOGLUE® adhesive or a fibrin glue, however, in other embodiments, the depth gauge may be coupled to the graft section using other known techniques. As shown in FIGS. 10 and 11, there is a small gap 56 between the bottom of the depth gauge and the base of the graft section. The gap 56 allows umbilical tape to be applied to the outside of the graft section after the cannula has been inserted into the heart to maintain the cannula in place.

The depth gauge is used in the following manner. First, in the manner described above, the patch section is attached to the heart, and an insertion tool is used to puncture the surface of the heart. Next, the cannula is pushed through the graft section. As best seen in FIG. 11, when the cannula is pushed into the heart, the seal 40 between the cannula and the graft section is lowered into the depth gauge. Since the depth gauge is transparent, the surgeon is able to see how far the cannula has been moved into the heart based on the distance "d" between the top of the depth gauge and the seal 40. Once the cannula is at the proper depth, umbilical tape is used at gap 56 to secure the cannula in place. In one embodiment, the depth gauge may include markings to assist a surgeon in ensuring that the cannula has been inserted a desired amount. To remove the cannula of the cannula assembly 52, the umbilical tape is removed, and the cannula is withdrawn in the manner described above.

In cannula assemblies 31 and 52 described above, a seal between the cannula and the sewing cuff is accomplished using a fixed seal that permanently attaches the graft section of the sewing cuff to the cannula. In another embodiment, which will now be described with reference to FIG. 12, a cannula assembly 60 is provided in which the cannula 33 couples to the sewing cuff 32 using a slideable seal that allows the cannula to be moved with respect to the graft section when the cannula is implanted into and removed from the heart. In cannula assembly 60, the cannula 33 is coupled to the graft section 36 of the sewing cuff 32 using a compression seal 62. The compression seal may be implemented using, for example, a simple silicone ring attached to the graft section pressing on the outside perimeter of the cannula.

In the cannula assembly 60, the cannula 33 is implanted and removed in a manner similar to cannula assemblies 31 and 52 discussed above, except that in the cannula assembly 60, the cannula moves with respect to the retaining seal 62 as the cannula is inserted into the heart. Upon insertion, the cannula may be held in place using umbilical tape 64 as discussed above.

Another embodiment of a cannula system 65 will now be described with reference to FIG. 13 which shows a cross-sectional side view of the cannula system 65. The cannula system 65 is similar in some aspects to cannula systems described above, and includes a cannula 66 and a sewing cuff 68. The sewing cuff includes a patch section 70 and a graft section 72 that are coupled together in a manner similar to sewing cuffs described above. The graft section 72 includes a flange 74. The flange 74 extends around the top of the graft section and in one embodiment is made from a rigid plastic material, such as medical grade polycarbonate. The flange 74 may be coupled to the graft section using, for example glue, such as polyurethane or UV curable epoxy. In one embodiment, the flange 74 includes an external threaded surface 75 for mating with a coupling nut as described below.

The cannula 66 has a flange 76 that extends around the outside of the cannula at a location that is approximately three inches from the distal end of the cannula for a graft section that is three inches in length. The flange 76 may be a molded part of the cannula 66 or may be glued or fixed to the cannula using any other method. The cannula system 65 further includes a seal 78 disposed between flanges 74 and 76. The seal may be, for example, an elastomer seal that is used to prevent fluid leakage. The seal may be fixed to one of the flanges 74, 76, and contained in a groove. The cannula system also includes a coupling nut 80 that is used to couple the flanges 76, 78 together. The coupling nut includes a cylindrical section 82 and a retaining section 84. The cylindrical section has an internal threaded surface 85 for mating with the external threaded surface 75 of the flange 74.

The cannula system 65 is used as follows. Initially, the sewing cuff 68 is disconnected from the cannula 66 and the patch section 70 is attached to a vascular tissue, such as the surface 42 of the heart, in a manner similar to other patch sections described above. The cannula 66 is then coupled to the sewing cuff using the coupling nut 80 to secure the cannula to the sewing cuff. As the coupling nut is tightened, the seal 78 is compressed between the flanges 74 and 76. An insertion tool, like insertion tool 44 described above, may be inserted through the cannula 66 and the sewing cuff 68 and used to pierce the surface of the heart. The cannula can then be inserted through the surface of the heart with the graft section compressing to allow the cannula to move into the heart. Once positioned in the heart, umbilical tape can be used around the outside of the graft section to secure the cannula in place in the heart. Removal of the cannula 66 may be accomplished in a manner similar to cannula 33 discussed above.

In the cannula system 65, a coupling nut 80 is used to couple the flanges 74, 76. In other embodiments, other securing mechanisms or latches may be used in place of the coupling nut. Further, while the coupling nut is shown mounted on the flange 76 of the cannula 66, in other embodiments, the coupling nut may be mounted on the flange 74 of the sewing cuff, and the flange 76 on the cannula may be threaded to couple with the coupling nut.

Figure 14A:
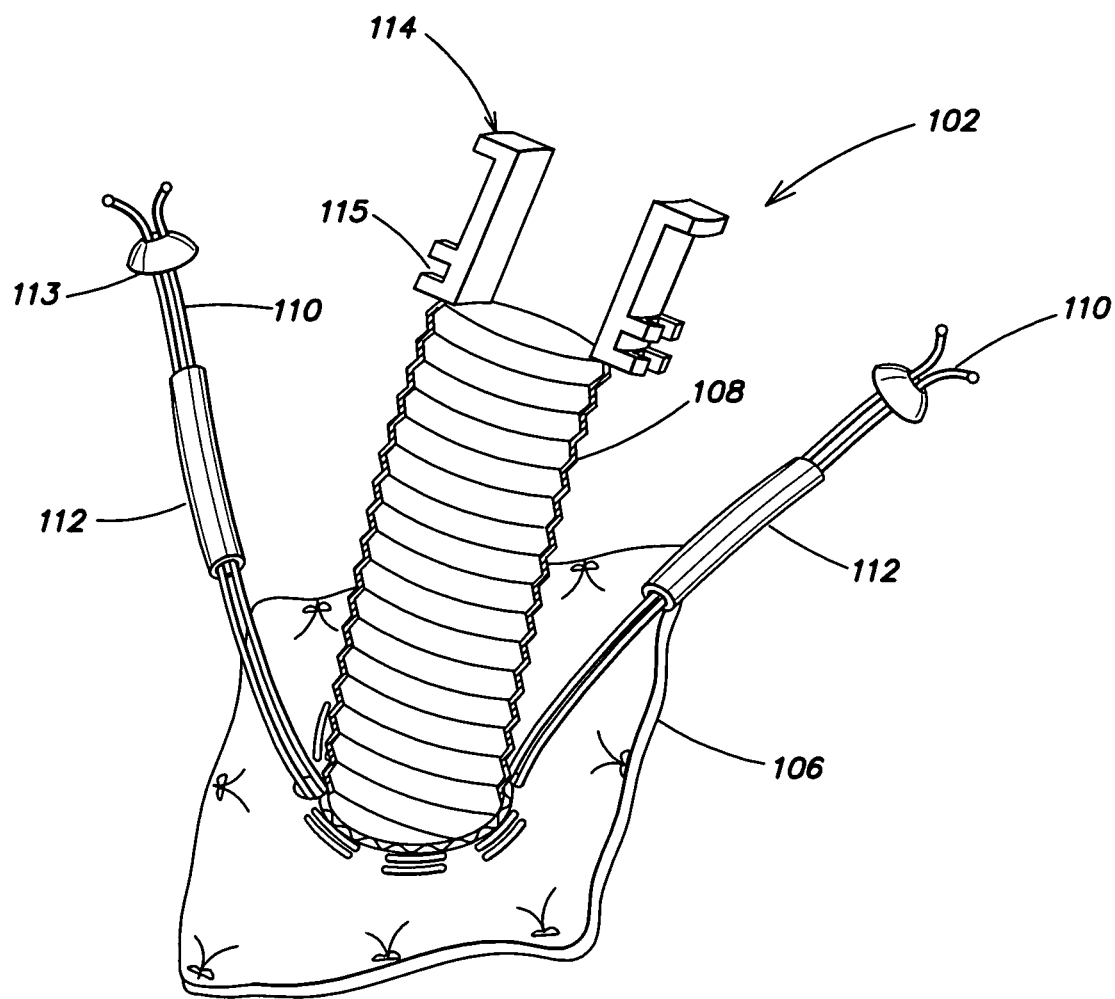
FIG. 14A is a perspective view of a sewing cuff in accordance with another embodiment.
Figure 14B:
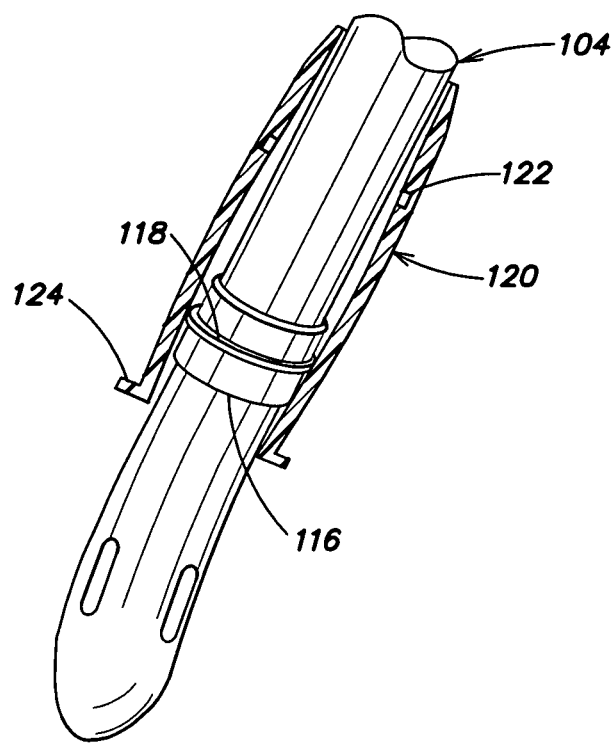
FIG. 14B is a perspective view of a cannula used with the sewing cuff of FIG. 14A in accordance with one embodiment.

Another embodiment of a cannula system 100 will now be described with reference to FIGS. 14A, 14B, 15A and 15B. The cannula system 100 includes a sewing cuff 102 (FIG. 14A) and a cannula 104 (FIG. 14B). The sewing cuff 102, like sewing cuff 20 includes a patch section 106 and a graft section 108. In addition, sewing cuff 102 includes double purse string sutures 110 that are coupled around the seam between the patch section and the graft section. Each of the sutures 110 includes a tourniquet 112, such as those available from Medtronic, Inc. of Minneapolis Minn., under part number 79004. The tourniquets are used to secure the sutures, as described below. Thermoplastic buttons 113 are located on the ends of the purse string sutures The graft section 108 also includes two flange sections 114 having channels 115. The flange sections may be made from rigid plastic and are secured to the top of the graft section 108 using, for example, glue. In place of two flange sections, one flange section that extends about the circumference of the top of the graft section may be used.

The cannula 104 used in the cannula system 100 is similar to cannula 33 discussed above, with the exception that cannula 104 includes a rigid cylindrical plastic section 116 having a ridge 118. The plastic section 116 may be glued to the external surface of the cannula 104 to hold the plastic section at a distance of approximately 2.5 inches from the distal end of the cannula. As described below, a snap collar 120 having an annular concave ring 122 and flanges 124 may be coupled around the outside of the cannula 104.

Figure 15A:
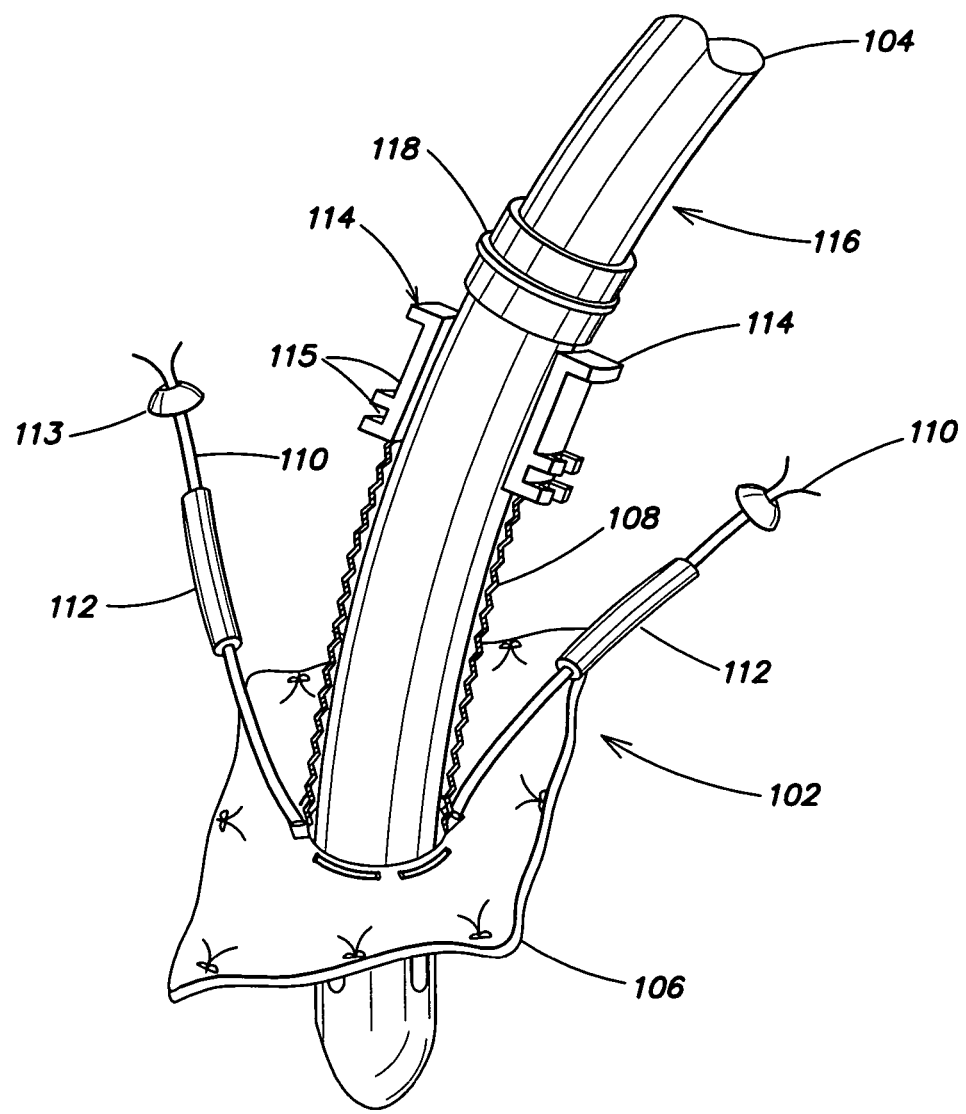
FIG. 15A is a perspective view of a cannula assembly incorporating the sewing cuff of FIG. 14A and the cannula of FIG. 14B.

Operation and use of the cannula system 100 will now be described with reference to FIGS. 15A and 15B. Initially, the patch section 106 is coupled to vascular tissue, such as a heart surface, in the same manner as other patch sections described above. The cannula 104 is then inserted into the sewing cuff, and the heart surface may be punctured using an insertion tool, such as tool 44 described above, by inserting the tool through the cannula. Piercing of the heart surface may be done prior to inserting the cannula into the sewing cuff. The cannula is then inserted into the heart, and the purse strings 110 and tourniquets 112 are used to secure the graft section to the cannula. Once the purse strings and tourniquets are tightened, the buttons 113 are snapped into the channels 115 of the flange sections 114 to keep the ends of the purse strings away from the cannula insertion site.

Figure 15B:
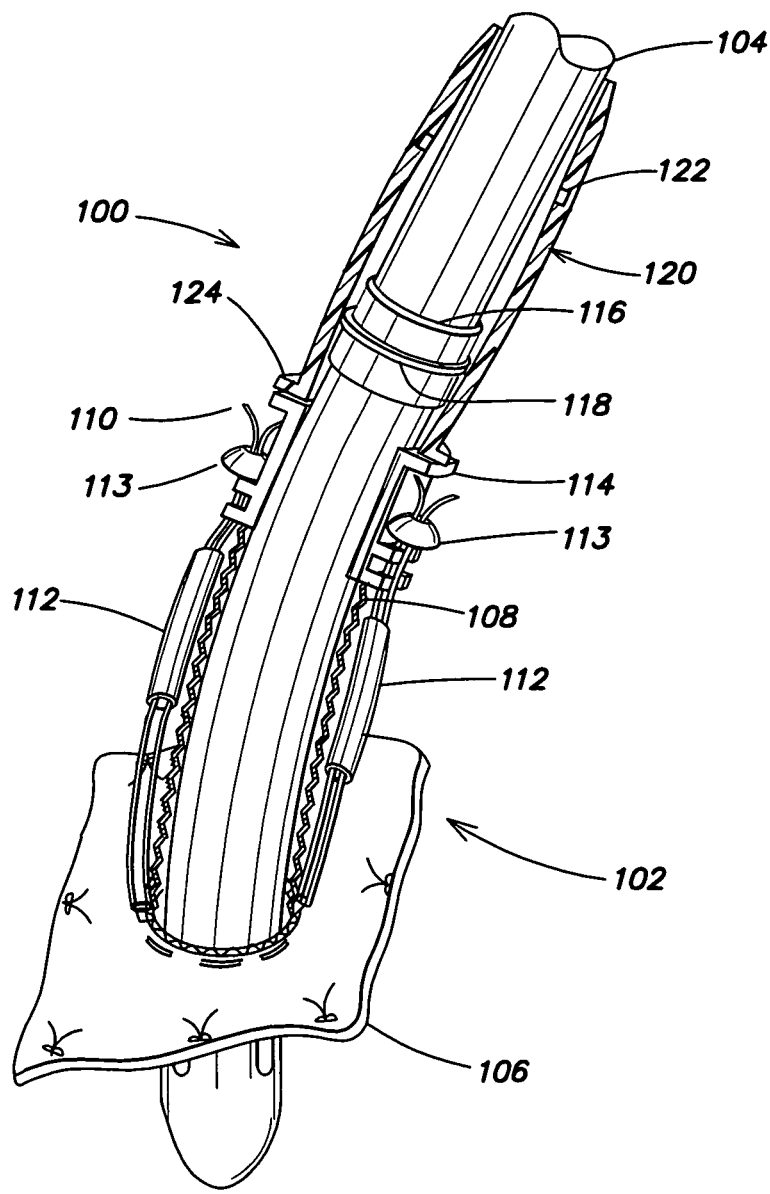
FIG. 15B is a cross-sectional view of the cannula assembly of FIG. 15A.

As shown in FIG. 15B, once the cannula 104 is inserted into the heart, the snap collar 120 may be installed around the outside of the cannula at the top of the graft section 108 of the sewing cuff. In one embodiment, the snap collar 120 is made from rigid plastic and includes two half-cylindrical sections that are coupled together around the outside of the cannula using clips, bands or other coupling techniques. In other embodiments, the snap collar may be a single cylindrical piece that is installed on the outside of the cannula prior to insertion and slid into place after insertion of the cannula into the heart. The snap collar 120 includes an annular concave ring 122 that, as described below, is used to capture the ridge 118 of the cannula to prevent the cannula from being completely withdrawn from the sewing cuff during explantation. In other embodiments, in place of the annular concave ring, a convex ring that contacts ridge 118 may be used. One advantage of using the concave ring is that the ridge and the ring may be sized such that the ridge "snaps" in place into the annular convex ring as the cannula is withdrawn. At least one of the snap collar 120 and the cannula 104 may have an elastomer o-ring to help maintain a fluid seal between the cannula and the snap collar.

To remove the cannula 104, the tourniquets are cut, and the cannula 104 is withdrawn until the ridge 118 snaps into the annular ring 122 indicating that the cannula has been fully withdrawn from the heart. The graft section may then be cut and stapled with the remainder of the cannula system 100 removed from the patient. The flanges 124 on the snap collar provide a surface against which force may be applied using one of a number of known tools, while the cannula is being withdrawn to prevent tension being applied to the sewing cuff which could cause the sewing cuff to be torn from the heart surface.

Figure 16:
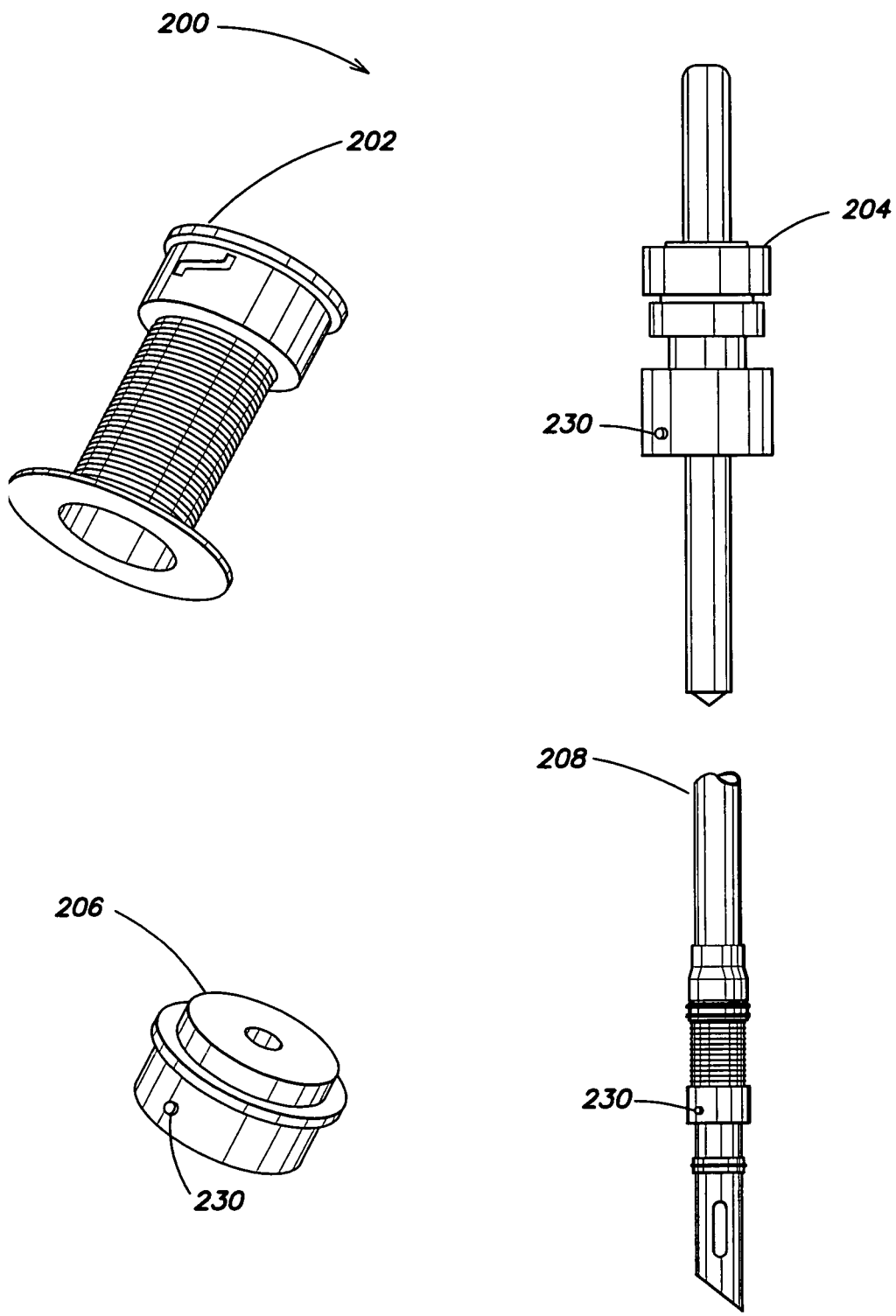
FIG. 16 is a perspective view of assemblies used in a cannula system in accordance with another embodiment.

A cannula system 200 in accordance with another embodiment of the invention will now be described with reference to FIG. 16. The cannula system 200 includes a sewing cuff 202, a stylet assembly 204, a pressure testing assembly 206 and a cannula assembly 208. As will be described below, each of the stylet assembly, the pressure testing assembly and the cannula assembly may be detachably coupled to the sewing cuff using in-line connectors. In use, and as further described below, the sewing cuff 202 is coupled to vascular tissue, such as the surface of the heart, in a similar manner to sewing cuff 20 discussed above. Once the sewing cuff is secured, the pressure testing assembly 206 may be coupled to the sewing cuff, pressurized saline solution may be introduced into the sewing cuff through the pressure testing assembly, and the integrity of the seal between the sewing cuff and the vascular tissue may be verified. The pressure testing assembly 206 is then decoupled from the sewing cuff, and the stylet assembly 204 is coupled to the sewing cuff. The stylet assembly 204 is used to make an insertion into the vascular tissue, and then the stylet assembly is decoupled from the sewing cuff 202. The cannula assembly 208 is then coupled to the sewing cuff 202 and the cannula is inserted through the incision made by the stylet assembly into, for example, the heart. The components of the system 200 may be packaged together with instructions for use of the system.

Figure 17A:
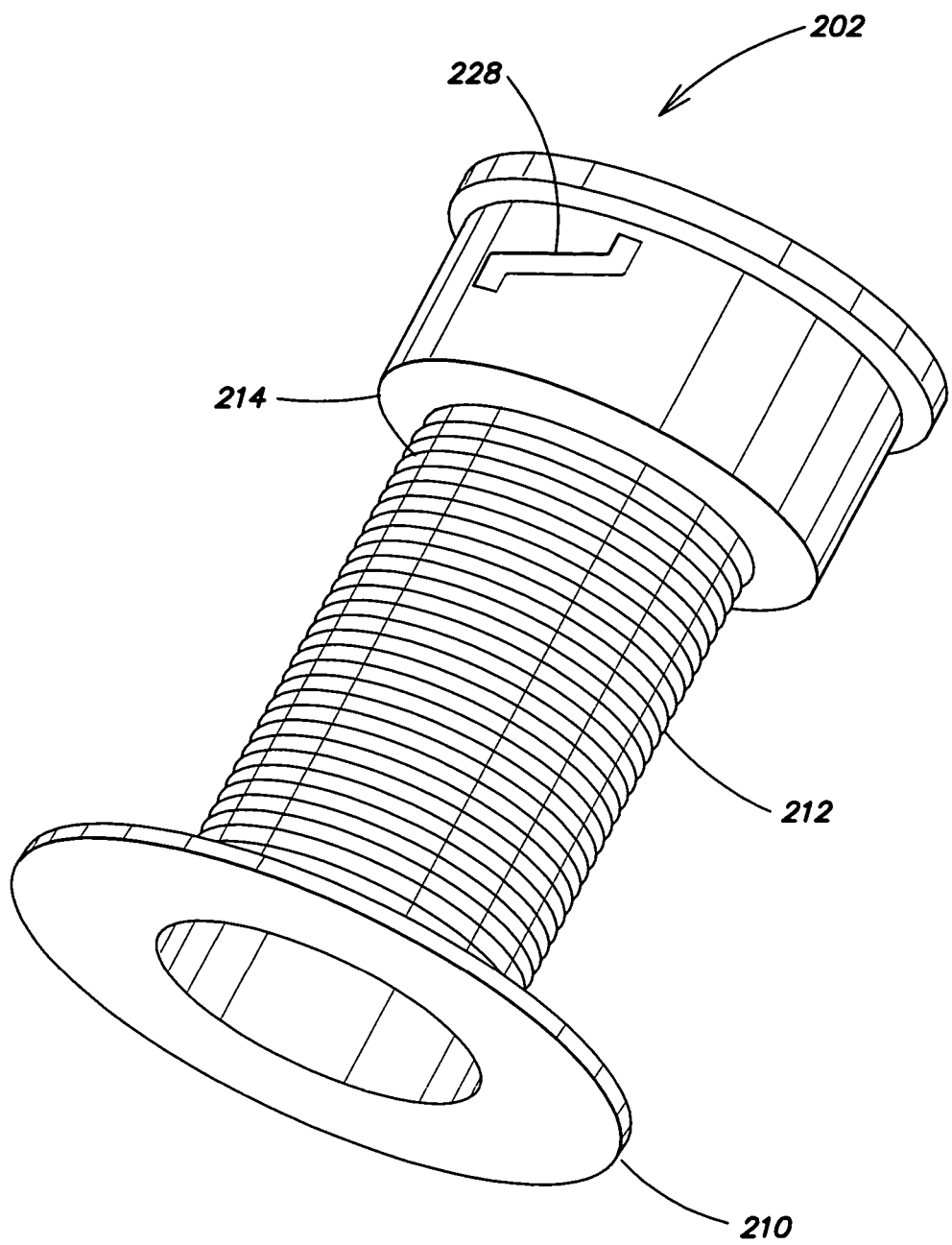
FIG. 17A is a perspective view of a sewing cuff used in the cannula system of FIG. 16.
Figure 17B:
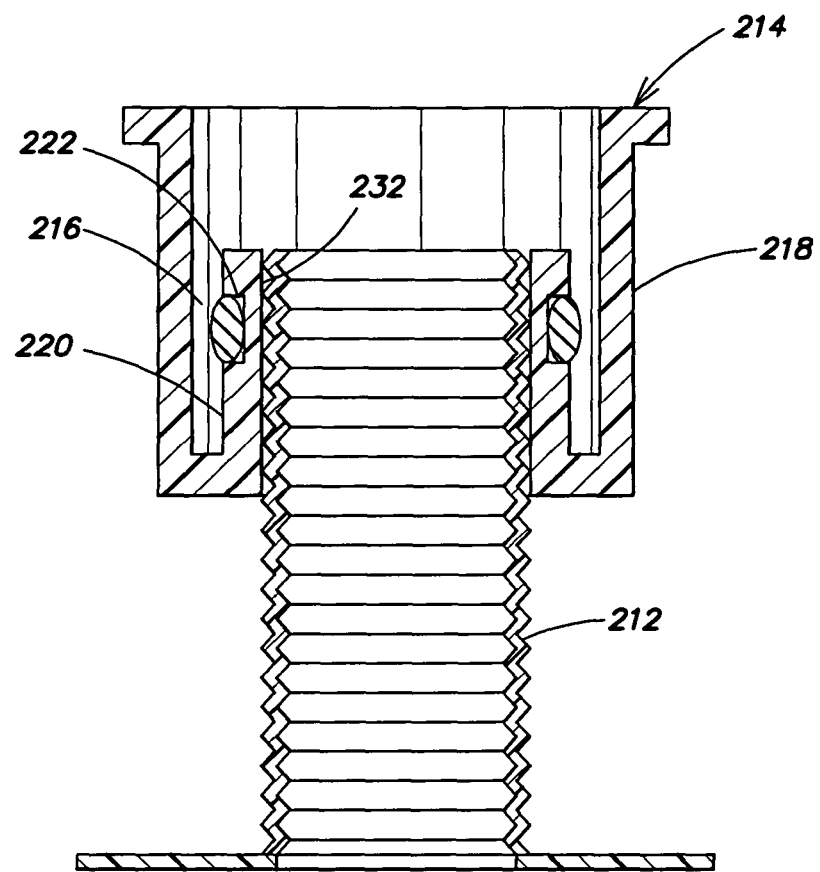
FIG. 17B is a cross-sectional side view of the sewing cuff of FIG. 17A.

As shown in FIGS. 17A and 17B the sewing cuff assembly 202 includes a patch section 210, a graft section 212, and a connector 214. The patch section 210 and the graft section 212 may be similar to those of the sewing cuff 20 described above, be of similar size and may be coupled together in the same manner.

The connector 214 is a twist-lock style female connector that mates with a twist-lock male connector contained on each of the stylet assembly 204, the pressure testing assembly 206 and the cannula assembly 208. The connector 214 has an o-ring 216 that is used to provide a fluid seal when coupled to the mating male connector. The connector 214 has an outer cylindrical portion 218 and an inner cylindrical portion 220. The inner cylindrical portion includes a groove 222 for retaining the o-ring 216. The connector 214 is designed such that a flange of the mating connector is inserted between the outer cylindrical portion 218 and the inner cylindrical portion 220 causing compression of the o-ring 216 between the flange of the male mating connector and the inner cylindrical portion 220 of the female connector. The outer cylindrical portion 218 has two grooves 228 for receiving a knob 230 of the male mating connector for securing the male mating connector to the female connector. One of the grooves 228 is shown in FIG. 17A and the other of the grooves 228 is positioned 180 degrees around the circumference of the outer cylindrical portion of the connector.

In one embodiment, the graft section 212 of the sewing cuff is glued to an inner surface 232 of the female connector 214, using, for example, polyurethane. However, in other embodiments other adhesives and techniques may be used to couple the graft section to the connector 214. In one embodiment, the connectors are made from polycarbonate however, in other embodiments other materials may be used for the connectors.

Figure 18:
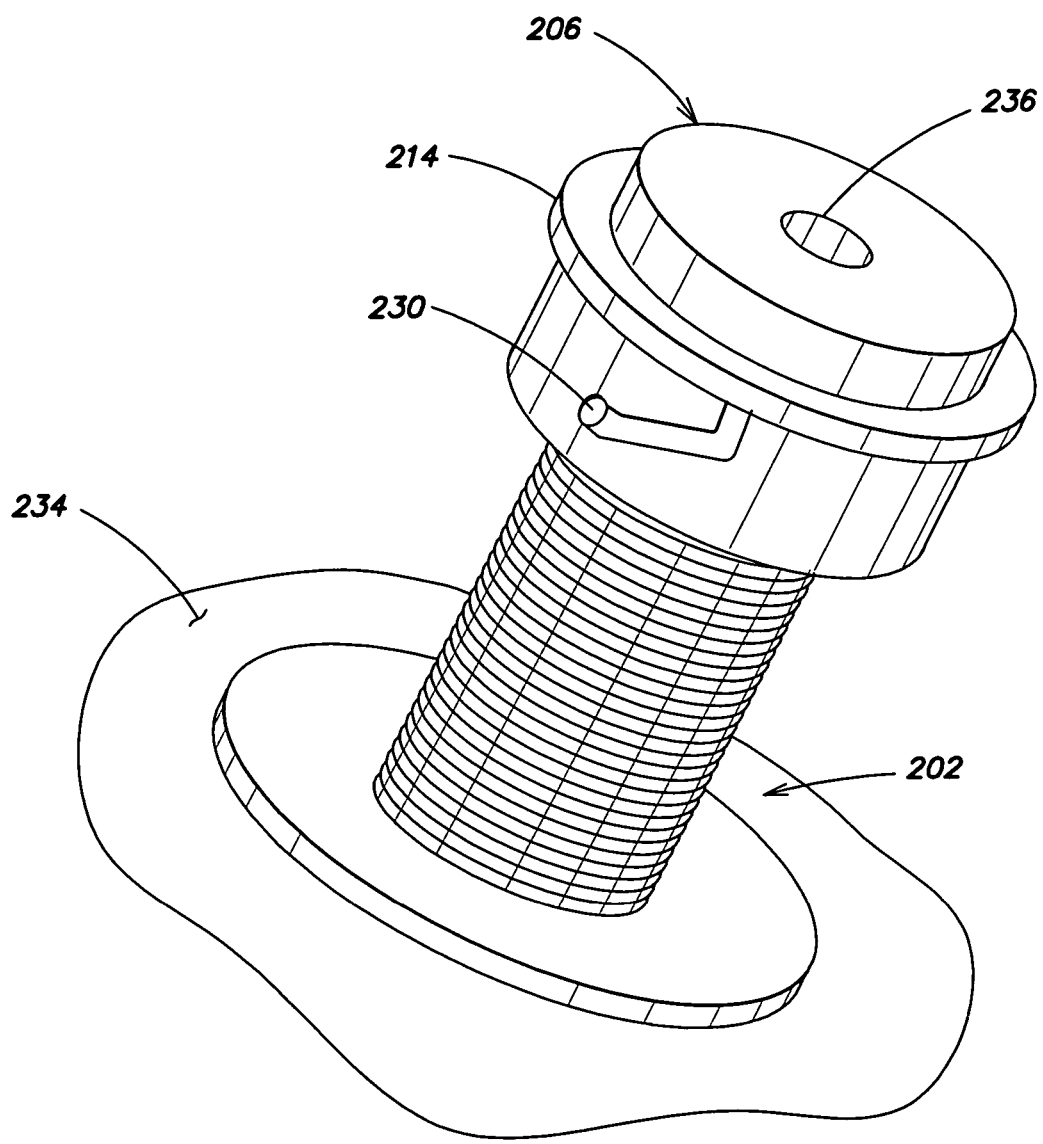
FIG. 18 is a perspective view of a pressure testing assembly of the cannula system of FIG. 16 coupled to the sewing cuff of FIG. 17A.

FIG. 18 shows a perspective view of the pressure tester assembly 206 coupled to the sewing cuff 202 with the sewing cuff coupled to a heart surface 234. In one embodiment, the pressure tester assembly is a one-piece assembly, constructed from polycarbonate, that incorporates the male mating connector. The pressure tester assembly includes a top portion having a female luer connector 236 incorporated therein.

In use, after the sewing cuff 202 has been secured to the heart, or some other vascular surface, the male connector of the pressure tester assembly is coupled to the female connector of the sewing cuff 202. A male luer connector of a pressurized source of saline solution is coupled to the female luer connector and a pressurized saline solution is injected through the luer connector and into the sewing cuff. In one embodiment, a syringe filled with saline solution may be used as the pressurized source. The integrity of the seal between the sewing cuff and the heart is verified by applying pressurized saline. The particular pressure applied is within the surgeon's discretion, but may be on the order of about 150 mmHg. If any leaks in the seal are detected, the suturing (or other sealing methods) may be further secured and the seal may be retested prior to insertion of the cannula. After the integrity of the seal is verified, the pressure tester assembly is decoupled from the sewing cuff.

Figure 19:
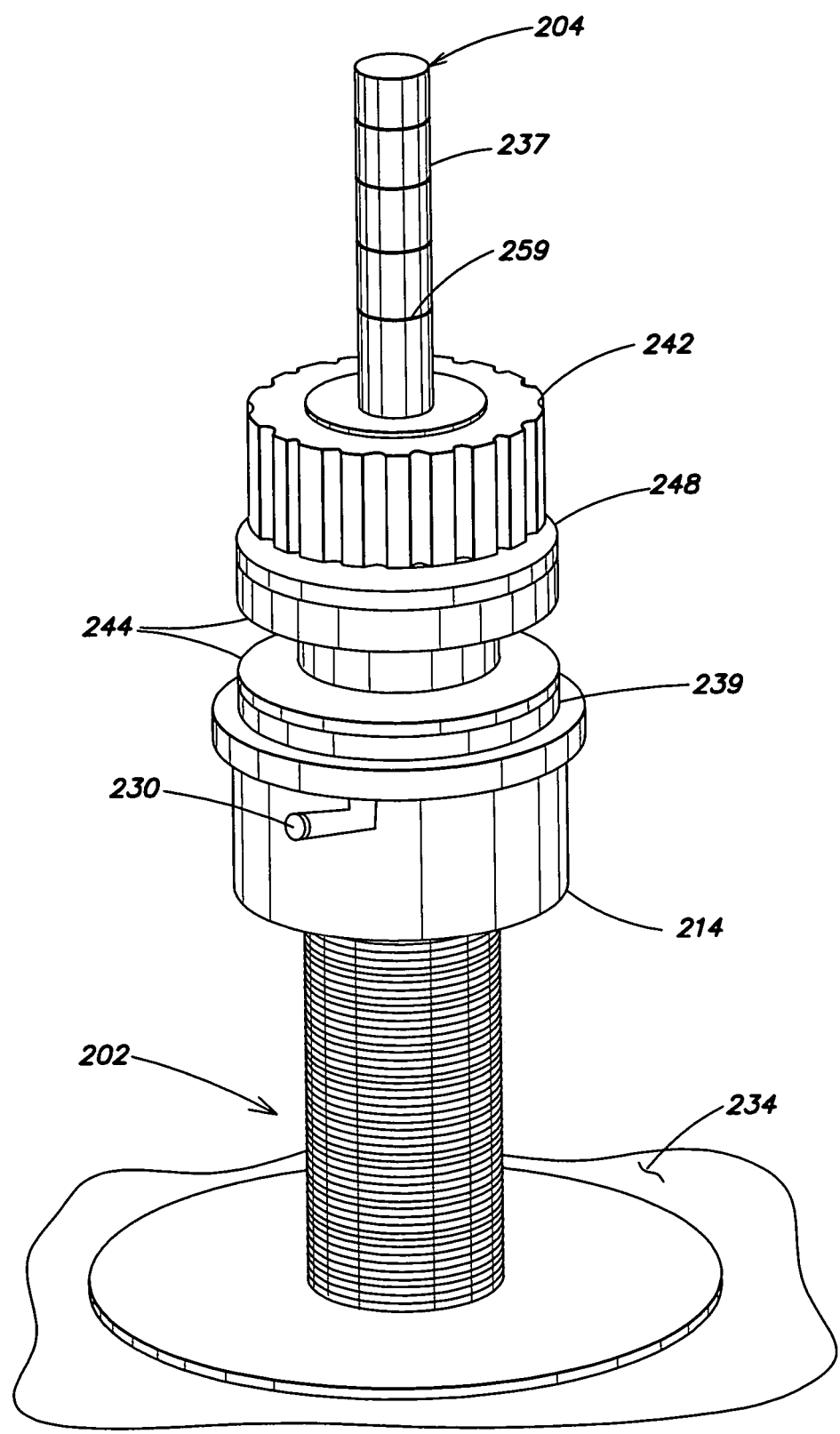
FIG. 19 is a perspective view of a stylet assembly of the cannula system of FIG. 16 coupled to the sewing cuff of FIG. 17A.
Figure 20:
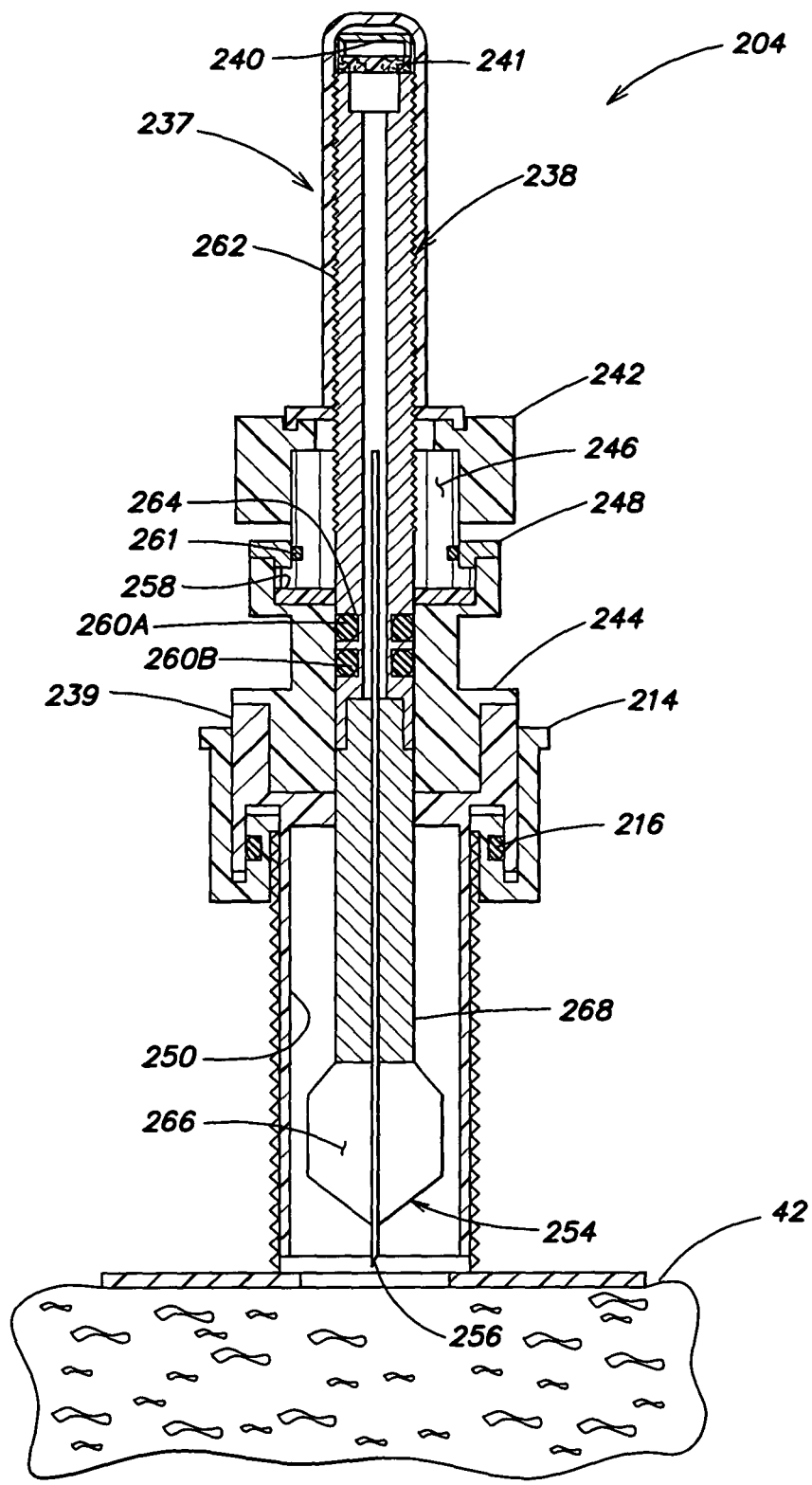
FIG. 20 is a cross-sectional view of the stylet assembly and sewing cuff of FIG. 19.
Figure 21:
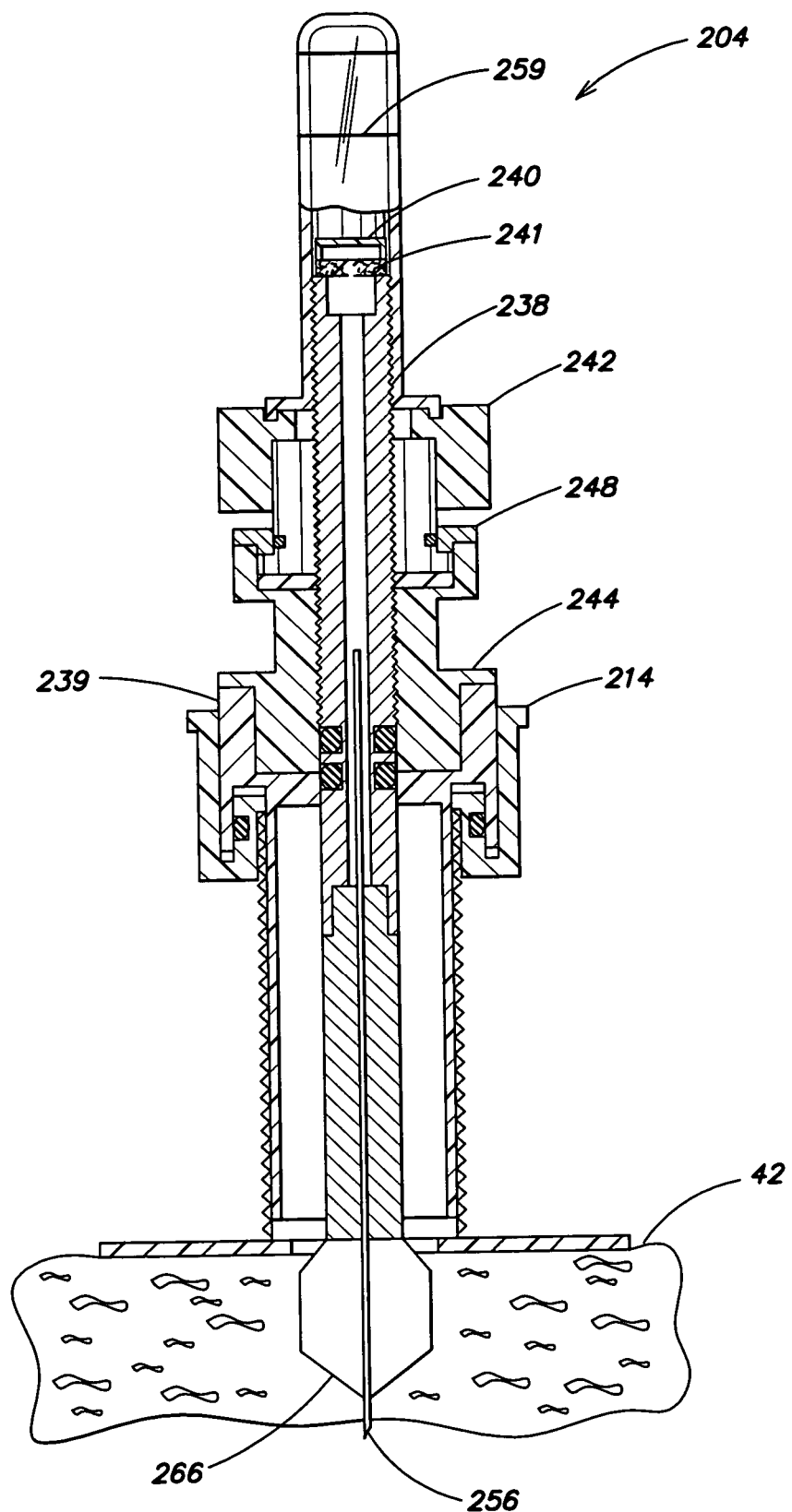
FIG. 21 is a cross-sectional view of the stylet assembly and sewing cuff of FIG. 19 with blades of the stylet assembly in an extended position.

The construction and operation of the stylet assembly 204 will now be described in further detail with reference to FIGS. 19-21. FIG. 19 is a perspective view of the stylet assembly 204 coupled to the sewing cuff with the sewing cuff coupled to the heart surface 234, FIG. 20 is a cross-sectional view of the stylet assembly in a retracted position, and FIG. 21 is a cross-sectional view of the stylet assembly in an engaged position. The male connector 239 of the stylet assembly couples to the sewing cuff 202 in the same manner as the connector of the pressure tester assembly. The stylet assembly includes an upper body section 237, a plunger assembly 238 having a clear cap 240 with a hydrophobic membrane 241, a knob 242, a body 244, a nut 246, a nut retainer 248, a shroud 250, a blade assembly 254, a hypodermic needle 256, and a washer 258.

The upper body section 237 is coupled to the knob 242, is transparent and includes markings 259 that provide a visual indication of the relative location of the plunger assembly. The plunger assembly 238 is contained within the upper body section 237 and extends through the knob 242, the washer 258, the nut 246, and into the body 244. The distal end of the plunger assembly 238 includes a hollow cylindrical section that receives the blade assembly 254. The blade assembly may be glued or welded to the hollow cylindrical section. The external surface 262 of the plunger assembly is threaded to mate with threads contained in the nut 246. The nut retainer 248 is bonded to the body 244 using, for example, an adhesive, and the nut retainer holds the nut 246 in place. The washer 258 is located between the nut and the body 244 and is made of a low-friction material such as TEFLON®. The nut 246 extends into the knob, and is bonded to the knob, using, for example, an adhesive or set screw. The plunger assembly includes grooves 264 to receive O-rings 260A and 260B. The O-rings provide a fluid seal between the plunger assembly 238 and the body 244, and may be implemented using, for example, an elastomer o-ring. An elastomer o-ring 261 is also included in a groove of the nut 246.

The connector 239 of the stylet assembly includes an extended portion that functions as a shroud 250 that protects the graft section 212 from the blades. In the embodiment shown in FIG. 20, the shroud extends the length of the graft section of the sewing cuff.

The hypodermic needle 256 extends from the end of the blade assembly 254 to the clear cap 240 in the plunger assembly. In one embodiment, the hypodermic needle is implemented using one of a number of known devices. In one embodiment, the clear cap is implemented using a hollow cylindrical plastic section, and as described below, the cap fills with blood when the hypodermic needle has penetrated through the heart tissue and into the ventricle. One end of the clear cap is coupled to the hypodermic needle, the other end is covered by the hydrophobic membrane 241. The hydrophobic membrane allows air to escape the hypodermic needle as it is filled with blood.

The blade assembly 254 includes a set of four blades 266 coupled to a blade shaft 268. In one embodiment, the blades 266 and the blade shaft 268 are made from surgical steel however, in other embodiments, other materials may be used. In one embodiment, each of the blades has a width of 0.525 inches and a length of 1.25 inches.

Operation of the stylet assembly will now be further described. As discussed above, the stylet assembly may be mated to the female connector 214 of the sewing cuff 202. When coupled to the sewing cuff, the blade assembly housing 252 extends through the graft section 212 of the sewing cuff. When initially coupled to the sewing cuff, the blades 266 are in a retracted position in the blade assembly housing. To pierce the surface of the heart, the knob 230 is rotated causing the plunger assembly and the blades to be lowered to and through the heart surface. The knob 230 rotates with respect to the body 244, and the upper body section, and the nut 246 rotate with the knob. The plunger assembly has one or more stops that prevent it from rotating with the knob and the interaction between the threads on the nut and the threads on the plunger assembly cause the plunger assembly to move up and down with rotation of the knob. The markings 259 can be used to monitor the insertion of the blades. Further, once the tip of the blades penetrates the heart tissue and enters the ventricle, blood will flow through the hypodermic needle 256 and be visible in the cap 240. In one embodiment, once blood appears in the cap 240, the knob 230 is advanced one additional full turn, which causes the blades to move an additional half inch and fully pierce the heart and enter the ventricle. The use of the hypodermic needle along with the cap and markings allows a surgeon to carefully monitor insertion of the blades to ensure that the heart tissue is fully penetrated and that the blades do not extend too far into the ventricle.

After the blades have fully penetrated the heart tissue, the knob 230 is turned in the opposite direction to cause the plunger to move upward to retract the blades back into the blade housing. The retraction of the blades can be monitored using the markings 259 in the upper body housing. Once the blades have been fully retracted, the graft section of the sewing cuff may be extended and a clamp can be applied to the graft section below the blade assembly housing to clamp off the graft section. In one embodiment, a surgical hemostat can be used to clamp the graft section. Once the clamp is in place, the connector of the stylet assembly may be disconnected from the connector of the sewing cuff to remove the stylet assembly. Once the stylet assembly is decoupled from the sewing cuff, the cannula assembly 208 is coupled to the sewing cuff, and the clamp may be removed from the graft section.

Figure 22:
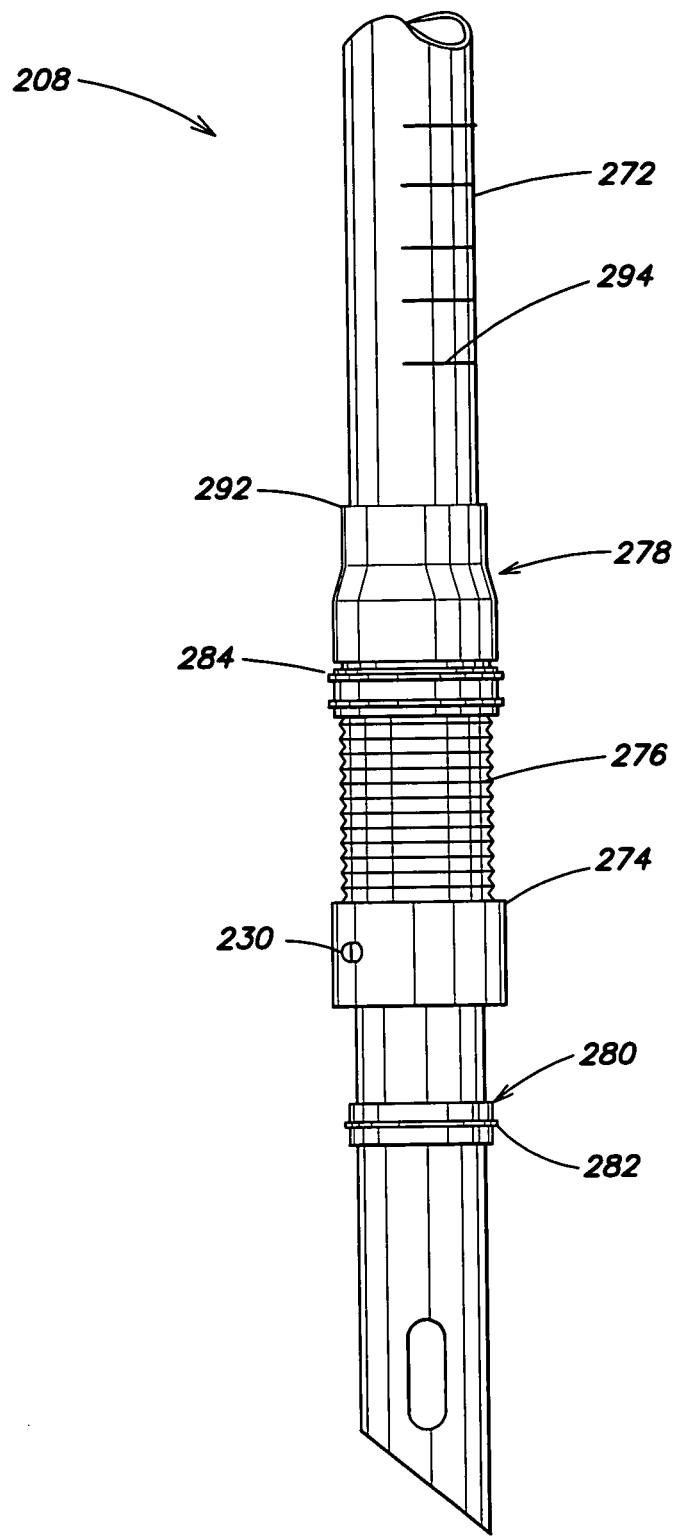
FIG. 22 is a side view of a cannula assembly used in the cannula system of FIG. 16.

The cannula assembly 208 will now be described with reference to FIGS. 22-24. The cannula assembly 208 includes a cannula 272, a cannula connector 274, a cannula graft section 276 and a sliding seal assembly 278. The cannula 272 in one embodiment is implemented using a 42 Fr atrio-ventricular cannula. The cannula 272 has a rigid section 280 having a ridge 282 both of which are similar to the rigid plastic section 116 and ridge 118 of cannula 104 described above. In one embodiment, the rigid section is glued to the cannula at a distance of approximately 1.5 inches from the distal end of the cannula.

The cannula connector 274 is similar to and operates in the same manner as the connectors on the pressure tester and the stylet assembly described above and mates with the connector 214 of the sewing cuff 202. The cannula graft section 276 extends from the cannula connector 274 to the sliding seal assembly 278. The cannula graft section in one embodiment is fabricated from the same material as the graft section 212 of the sewing cuff, and the cannula graft section is glued to the cannula connector 274 and to the sliding seal assembly 278 using one of the glues described above. In some embodiments of the present invention, the graft section 276 may not be included and the sliding seal assembly may be coupled directly to the cannula connector 274. However, the use of the graft section 276 may provide an advantage in embodiments by adding flexibility to the cannula assembly.

Figure 23:
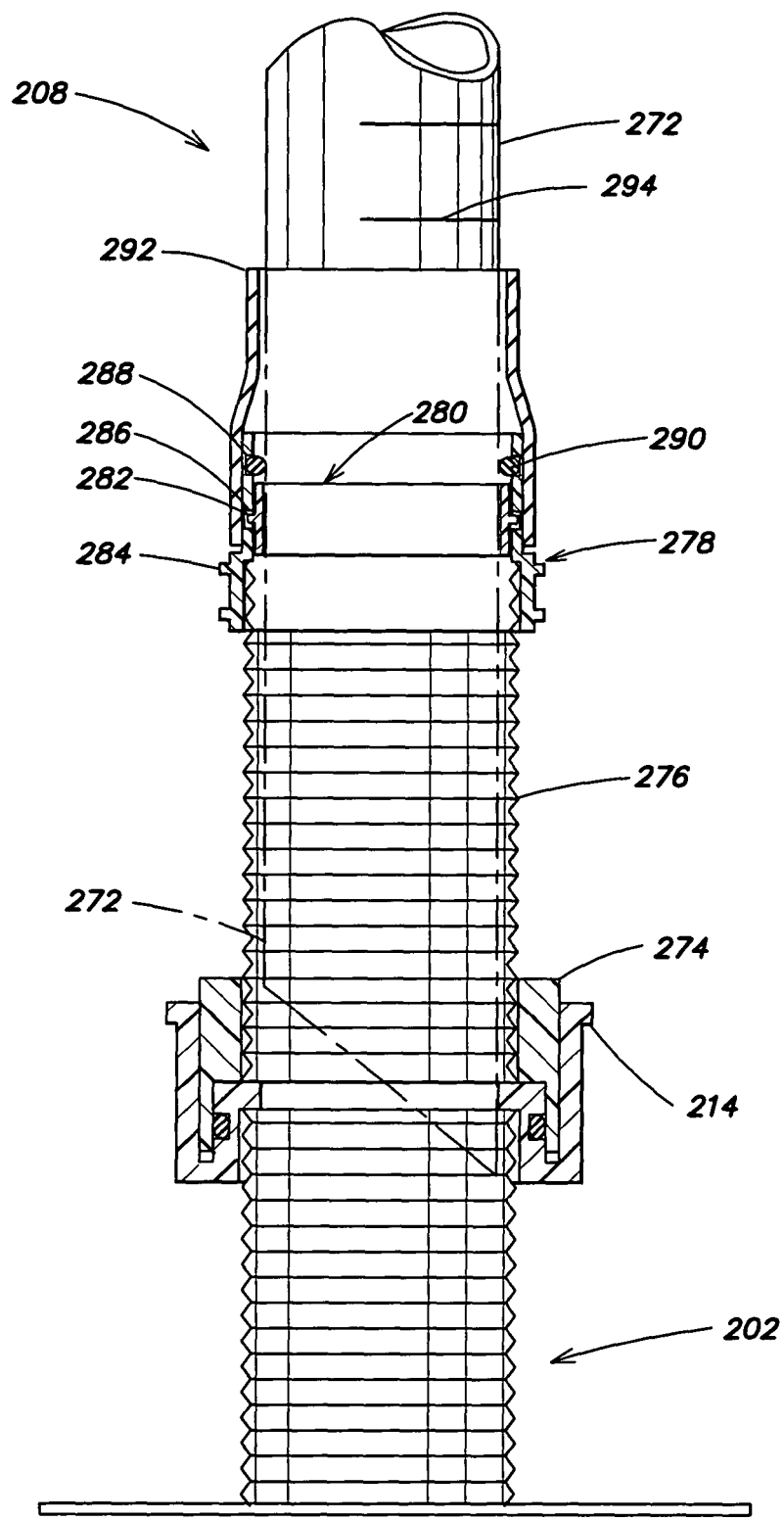
FIG. 23 is a cross-sectional side-view of the cannula assembly of FIG. 22.
Figure 24:
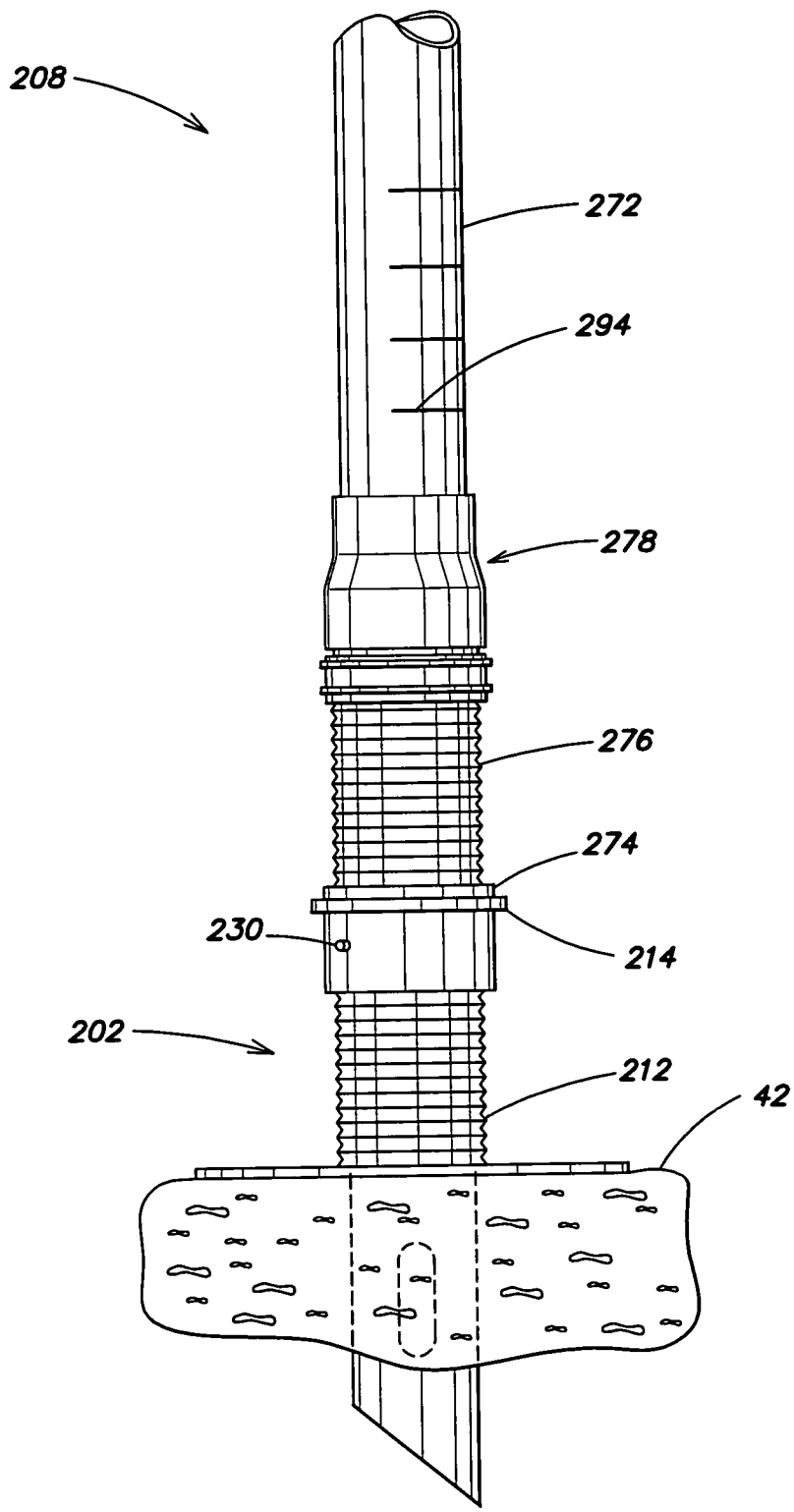
FIG. 24 is perspective view of the cannula assembly of FIG. 22 coupled to the sewing cuff of FIG. 17A.

The sliding seal assembly 278 is shown in greater detail in the cross-sectional view of FIG. 23. The sliding seal assembly includes a plastic shell 284 an elastomer o-ring 290 and a transition section 292. In one embodiment, the plastic shell is made from polycarbonate and the transition section 292 may be made from silicone, however, in other embodiments other materials may be used. The plastic shell includes an annular ring 288 that contains the o-ring 290. The o-ring is used to provide a fluid seal between the plastic shell and the outer surface of the cannula. The plastic shell also includes an annular detent 286 that is configured to receive the ridge 282 of the cannula 272 to prevent the cannula 272 from being completely withdrawn from the sliding seal assembly and operates in a manner similar to that of cannula system 100 described above.

After the stylet assembly 204 is decoupled from the sewing cuff 202, the cannula assembly 208 is coupled to the connector of the sewing cuff. When initially coupled to the sewing cuff, the cannula is withdrawn in the cannula assembly such that the ridge 282 is in the detent 286 of the sliding seal assembly. In one embodiment, with the cannula in the withdrawn position within the sewing cuff, the distal end of the cannula is contained within the cannula assembly and does not extend into the graft section of the sewing cuff. However, in other embodiments, the cannula may extend into the graft section. After the cannula assembly has been coupled to the sewing cuff, the clamp, previously placed on the graft section of the sewing cuff prior to removal of the stylet assembly, may be removed. After removal of the clamp, the cannula may be slid through the graft section of the sewing cuff and into the ventricle. In one embodiment, the cannula 272 includes markings 294 that allow a surgeon installing the cannula to determine when the cannula has been inserted into the ventricle. In one embodiment, in which the graft section is 2.5 inches long, the cannula 272 is inserted approximately two inches to install it in the ventricle. After installation of the cannula, the patient's chest cavity may be closed, and the cannula along with an implanted outflow cannula may be coupled to a ventricle assist device to provide external ventricular assistance for the patient.

As discussed above, the use of a ventricular assist device can have the positive result of allowing the patient's heart to sufficiently recover, such that the VAD is no longer needed. In the past, removal of the inflow cannula has typically required reopening of the patient's chest cavity resulting in risk to the patient and a relatively long recovery time. With embodiments of the invention, as will now be further described, the inflow cannula 272, as well as other cannulae discussed above, may be removed using minimally invasive surgical techniques that do not require reopening of the chest cavity. In one embodiment, the cannula 272 is removed by sliding the cannula with respect to the sliding seal such that the cannula is withdrawn from the ventricle. The cannula is withdrawn until the ridge 282 snaps in place in the annular detent 286 of the plastic shell 284. At the point that the ridge is in the annular detent, the distal end of the cannula is substantially or completely withdrawn from the graft section of the sewing cuff. Using only small incisions in the chest, standard surgical instruments, such as those discussed above, may be used to cut and staple the graft section. Once the graft section has been cut, the cannula and the remainder of the sewing cuff can be removed from the patient.

Figure 25:
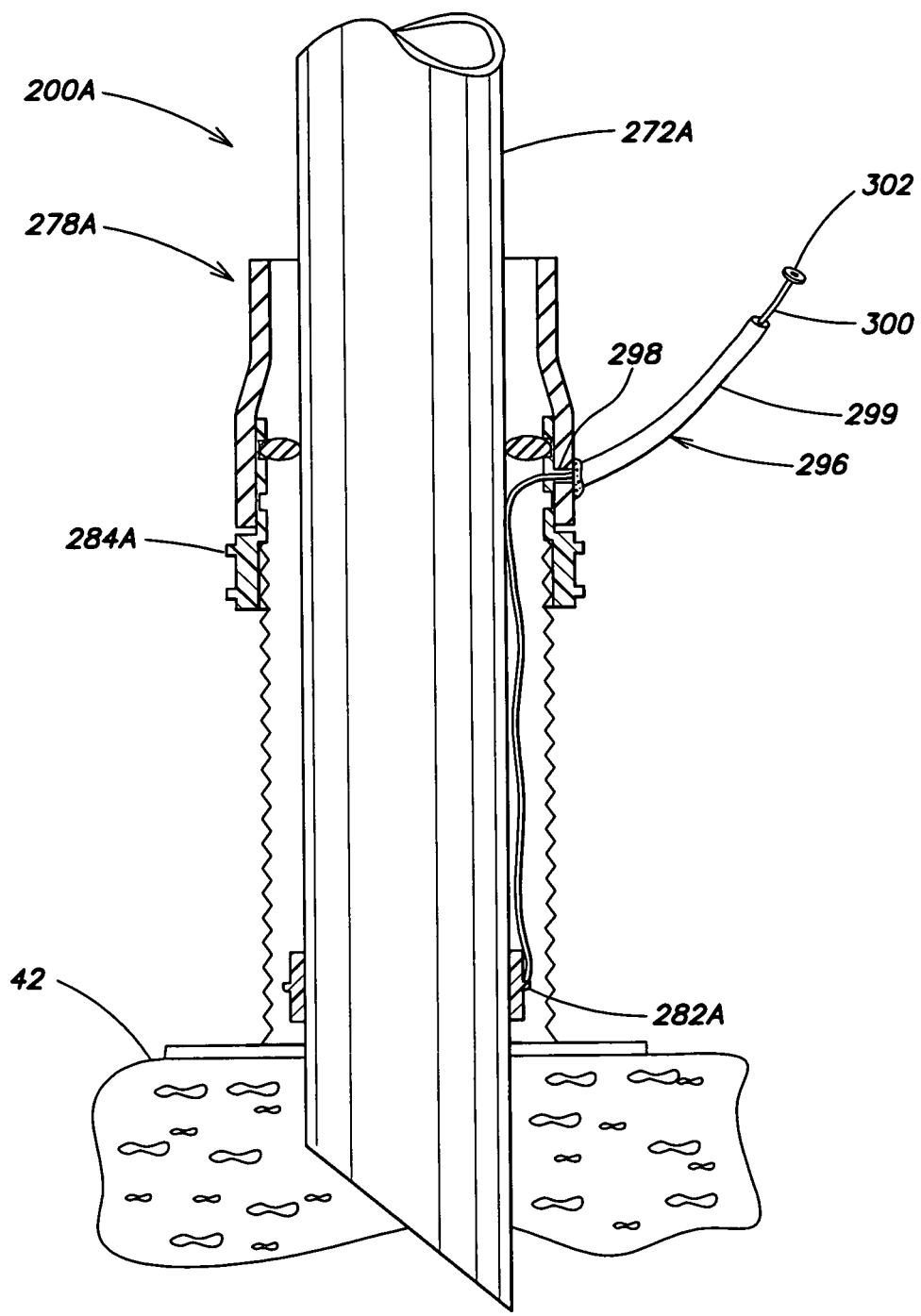
FIG. 25 is a cross-sectional side view of another embodiment of a cannula assembly.

In another embodiment, which will now be described with reference to FIG. 25, modifications are made to the cannula 272 and the sliding seal assembly 278, described above, to ease the process of withdrawing the cannula from the ventricle. In the embodiment shown in FIG. 25, each of the reference numbers for the modified parts have the same base reference number as those used with cannula system 200, except that a suffix "A" is added to each reference number of the modified system.

The major modification provided to the cannula system 200A of FIG. 26, is that a retraction cord 296 is added to the system. The retraction cord 296 is attached to an opening 298 in the plastic shell 284A on the distal side of the sliding seal assembly 278A. The retraction cord includes an outer jacket 299 having a coaxial inner cable 300. In one embodiment, the outer jacket is made from polyurethane and the inner cable 300 is made from surgical steel, however other suitable materials may also be used. The outer jacket of the retraction cord is sealed to the plastic shell 284A at the opening 298, such that the outer jacket provides a seal over the opening with the coaxial inner cable 300 passing through the opening. The coaxial inner cable is coupled to the ridge 282A of the cannula 272A using, for example, a steel connecting clip. As shown in FIG. 25, the inner coaxial cable extends out of the end of the outer jacket, and the proximal end of the inner coaxial cable may include a small loop 302 or other device that functions as a handle to allow a surgeon to grasp the inner cable to retract the cannula 272A as described below. A seal, through which the coaxial inner cable can slide, may be provided at the proximal end of the outer jacket 299.

Operation of the cannula system 200A is similar to that of cannula system 200 described above, with the exception of the process for withdrawing the cannula from the ventricle. In the cannula system 200A, the cannula 272A is withdrawn by pulling on the loop 302 to withdraw the cannula 272A from the ventricle. As with other embodiments described above, the cannula 272A is withdrawn until the ridge 282A snaps into the annular detent of the plastic shell. Once the cannula 272A is withdrawn, the sewing cuff may be cut and clamped as described above. The use of the retraction cord in the cannula system 200A may offer additional advantages of allowing the cannula 272A to be withdrawn with less pressure applied to the sewing cuff, reducing the risk of the sewing cuff being torn from the ventricle.

At least one embodiment described above provides advantages over prior art cannula systems, by providing a system that may be installed in a controlled manner with reduced risk of blood loss and removed using minimally invasive surgical techniques without the need for a sternotomy. While particular examples of embodiments have been described for use with left ventricle assist devices, embodiments of the invention are not limited to such use and may be used with right ventricle assist devices, and may be used in conjunction with other organs as well. Further, although primarily described for use as or with an inflow cannula, methods and apparatus of embodiments of the invention may be used with or as an outflow cannula, or for other uses as well.

In at least one embodiment described above, saline solution under pressure is applied to a sewing cuff to determine the integrity of a seal between the sewing cuff and vascular tissue. In other embodiments, other fluids and or gases under pressure may be used in place of the saline solution.

In at least one embodiment described above, the term stylet assembly is used to refer to an assembly used in a cannula system that includes a set of blades for piercing the surface of vascular tissue. As readily understood by one skilled in the art based on this disclosure, stylet assemblies used with embodiments of the invention may include various configurations of blades and/or other cutting instruments and are not limited to those described above. Further, at least one embodiment provides the advantage of off-pump insertion and removal of cannula systems.

In embodiments of the present invention, the term cannula is used to describe a tube capable of carrying fluids, for example, from the heart to an external device, such as a VAD. The term cannula as used herein and in the claims is not limited to any particular type of tube or for any particular purpose.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A cannula system comprising a cuff having a first section configured to couple to vascular tissue, the first section including an opening, the cuff further having a second section coupled to the first section, wherein the second section includes a compressible, elongated section composed of a graft material, the compressible elongated section having an inner portion;

a cannula coupled to the cuff via a seal between the cannula and the second section of the cuff, the cannula fixed to a portion of the second section of the cuff and movable with respect to the first section of the cuff such that compression of the second section of the cuff permits a distal end of the cannula to move from the inner portion of the second section of the cuff through the opening in the first section of the cuff; and a depth gauge coupled to the second section of the cuff such that the seal between the cannula and the second section of the cuff is moveable with respect to a portion of the depth gauge, wherein the depth gauge is coupled to the second section of the cuff such that a gap is between the depth gauge and the first section of the cuff;

wherein the depth gauge includes a transparent tube positioned over the second section of the cuff; and wherein the depth gauge includes a plurality of markings.

2. The cannula system of claim 1 wherein the seal includes an adhesive.

3. The cannula system of claim 1, wherein the cuff includes felt.

4. The cannula system of claim 1, wherein the second section includes pleats.

* * * * *